US010792210B2

(12) United States Patent
Goldfarb et al.

(10) Patent No.: US 10,792,210 B2
(45) Date of Patent: Oct. 6, 2020

(54) MOVEMENT ASSISTANCE DEVICE

(71) Applicant: VANDERBILT UNIVERSITY, Nashville, TN (US)

(72) Inventors: Michael Goldfarb, Franklin, TN (US); Ryan J. Farris, Nashville, TN (US); Hugo A. Quintero, Irvine, CA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 622 days.

(21) Appl. No.: 15/627,959

(22) Filed: Jun. 20, 2017

(65) Prior Publication Data
US 2017/0281453 A1 Oct. 5, 2017

Related U.S. Application Data

(63) Continuation of application No. 14/049,494, filed on Oct. 9, 2013, now Pat. No. 9,682,006, which is a
(Continued)

(51) Int. Cl.
A61H 3/00 (2006.01)
A61G 7/10 (2006.01)
(Continued)

(52) U.S. Cl.
CPC ............ A61H 3/00 (2013.01); A61G 7/1017 (2013.01); A61H 1/0262 (2013.01);
(Continued)

(58) Field of Classification Search
CPC .......... A61H 3/00; A61H 1/0262; A61H 3/02; A61H 3/04; A61H 2201/10;
(Continued)

(56) References Cited

U.S. PATENT DOCUMENTS 6,666,796 B1 12/2003 MacCready, Jr.
2003/0093021 A1 5/2003 Goffer
(Continued)

FOREIGN PATENT DOCUMENTS

| AU | 729913 | 2/2001 |
| EP | 1260201 | 11/2002 |
| WO | 2006074029 | 7/2006 |

OTHER PUBLICATIONS

Dollar et al., "Lower extremity exoskeletons and active orthoses: Challenges and State-of-the-Art", IEEE Transactions on Robotics (Feb. 1, 2008) 24(1): 144-158.
(Continued)

Primary Examiner — Quang D Thanh
(74) Attorney, Agent, or Firm — Nixon Peabody LLP

(57) ABSTRACT

A apparatus includes an a exoskeleton system with a plurality of sensors for generating signals indicating a current motion and a current arrangement of at least the exoskeleton system, a hip segment, and at least one lower limb. The lower limb includes thigh and shank segments for coupling to a lateral surface of a user's leg. The thigh segment includes a first powered joint coupling the thigh segment to the hip segment, a second powered joint coupling the thigh segment to the shank segment, and a controller coupled to the sensors, the first powered joint, and the second powered joint. The controller is configured for determining a current state of the exoskeleton system and a current intent of the user based on the signals and generating control signals for the first and second powered joints based on the current state and the current intent.

17 Claims, 19 Drawing Sheets

Related U.S. Application Data continuation-in-part of application No. 13/876,228, filed as application No. PCT/US2011/053501 on Sep. 27, 2011, now Pat. No. 9,693,926.

(60) Provisional application No. 61/386,625, filed on Sep. 27, 2010, provisional application No. 61/711,286, filed on Oct. 9, 2012.

(51) Int. Cl.

| | | |
|---|---|---|
| *A61N 1/04* | (2006.01) | |
| *A61H 1/02* | (2006.01) | |
| *A61N 1/36* | (2006.01) | |
| *A61G 5/14* | (2006.01) | |
| *A61H 3/02* | (2006.01) | |
| *A61H 3/04* | (2006.01) | |

(52) U.S. Cl.
CPC ............. *A61N 1/0452* (2013.01); *A61G 5/14* (2013.01); *A61G 7/109* (2013.01); *A61G 7/1096* (2013.01); *A61G 2203/36* (2013.01); *A61H 3/02* (2013.01); *A61H 3/04* (2013.01); *A61H 2201/10* (2013.01); *A61H 2201/1215* (2013.01); *A61H 2201/1463* (2013.01); *A61H 2201/164* (2013.01); *A61H 2201/165* (2013.01); *A61H 2201/1628* (2013.01); *A61H 2201/1676* (2013.01); *A61H 2201/5005* (2013.01); *A61H 2201/5007* (2013.01); *A61H 2201/5069* (2013.01); *A61H 2201/5084* (2013.01); *A61H 2201/5097* (2013.01); *A61N 1/36003* (2013.01)

(58) Field of Classification Search
CPC .... A61H 2201/1215; A61H 2201/1463; A61H 2201/1628; A61H 2201/164; A61H 2201/165; A61H 2201/1676; A61H 2201/5005; A61H 2201/5007; A61H 2201/5069; A61H 2201/5084; A61H 2201/5097; A61N 1/0452; A61N 1/36003; A61G 7/1017; A61G 7/109; A61G 7/1096; A61G 2203/36; A61G 5/14

See application file for complete search history.

(56) References Cited

U.S. PATENT DOCUMENTS

| | | | |
|---|---|---|---|
| 2004/0102723 A1 | 5/2004 | Horst | |
| 2004/0249319 A1* | 12/2004 | Dariush | A61H 1/00 601/5 |
| 2007/0203433 A1* | 8/2007 | Murphy | A61H 7/001 601/15 |
| 2008/0139968 A1* | 6/2008 | Endo | A61B 5/04888 600/595 |
| 2008/0234608 A1* | 9/2008 | Sankai | A61B 5/04888 601/5 |
| 2008/0249438 A1* | 10/2008 | Agrawal | A61H 1/0237 601/35 |
| 2009/0227925 A1 | 9/2009 | McBean et al. | |
| 2010/0121232 A1* | 5/2010 | Sankai | B25J 9/0006 601/23 |
| 2010/0217163 A1 | 8/2010 | Sankai | |
| 2012/0172770 A1* | 7/2012 | Almesfer | B25J 9/0006 601/35 |
| 2012/0259431 A1* | 10/2012 | Han | A61F 5/0125 623/24 |
| 2013/0231595 A1* | 9/2013 | Zoss | A61H 1/0255 601/34 |

OTHER PUBLICATIONS

Hwang et al., "Monitoring method of interactive torque between human and robot in exoskeleton systems", Rehabilitation Robotics (Jun. 23, 2009): 283-288.

Obinata et al., "Hybrid control of power orthosis and functional neuromuscular stimulation for restoring gait", IEEE Engineering in Medicine and Biology Society (Aug. 26, 2007): 4879-4882.

Pons, "Rehabilitation exoskeletal robotics", IEEE Engineering in Medicine and Biology (May 1, 2010) 29(3): 57-63.

Senanayake et al., "Emerging robotics devices for therapeutic rehabilitation of the lower extremity", Advanced Intelligent Mechatronics (Jul. 14, 2009): 1142-1147.

\* cited by examiner

600

MOVEMENT ASSISTANCE DEVICE

CROSS-REFERENCE TO RELATED APPLICATIONS

This application is a continuation of U.S. Non-provisional patent application Ser. No. 14/049,494, filed Oct. 9, 2013, which is a continuation-in-part of U.S. National Stage application Ser. No. 13/876,228, filed Mar. 27, 2013, which is a § 371 national stage entry of International Application No. PCT/US2011/053501, filed Sep. 27, 2011, which claims priority to U.S. Provisional Application No. 61/386,625, filed Sep. 27, 2010, the contents of all of which are hereby incorporated by reference. U.S. Non-provisional patent application Ser. No. 14/049,494, also claims priority to and the benefit of U.S. Provisional Application Ser. No. 61/711,286, filed Oct. 9, 2012, the contents of which is herein incorporated by reference in its entirety.

GOVERNMENT LICENSE RIGHTS

This invention was made with government support under NIH R01 HD059832-01/05 awarded by National Institutes of Health. The government has certain rights in the invention.

FIELD OF THE INVENTION

The present invention relates to field of powered assistive devices, and more specifically to powered assistive devices and methods.

BACKGROUND

There are currently about 262,000 spinal cord injured (SCI) individuals in the United States, with roughly 12,000 new injuries sustained each year at an average age of injury of 40.2 years. Of these, approximately 44% (5300 cases per year) result in paraplegia. One of the most significant impairments resulting from paraplegia is the loss of mobility, particularly given the relatively young age at which such injuries occur. Surveys of users with paraplegia indicate that mobility concerns are among the most prevalent, and that chief among mobility desires is the ability to walk and stand. In addition to impaired mobility, the inability to stand and walk entails severe physiological effects, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities.

In an effort to restore some degree of legged mobility to individuals with paraplegia, several lower limb orthoses have been developed. The simplest form of passive orthotics are long-leg braces that incorporate a pair of ankle-foot orthoses (AFOs) to provide support at the ankles, which are coupled with leg braces that lock the knee joints in full extension. The hips are typically stabilized by the tension in the ligaments and musculature on the anterior aspect of the pelvis. Since almost all energy for movement is provided by the upper body, these (passive) orthoses require considerable upper body strength and a high level of physical exertion, and provide very slow walking speeds. The hip guidance orthosis (HGO), which is a variation on long-leg braces, incorporates hip joints that rigidly resist hip adduction and abduction, and rigid shoe plates that provide increased center of gravity elevation at toe-off, thus enabling a greater degree of forward progression per stride. Another variation on the long-leg orthosis, the reciprocating gait orthosis (RGO), incorporates a kinematic constraint that links hip flexion of one leg with hip extension of the other, typically by means of a push-pull cable assembly. As with other passive orthoses, the user leans forward against the stability aid while unweighting the swing leg and utilizing gravity to provide hip extension of the stance leg. Since motion of the hip joints is reciprocally coupled through the reciprocating mechanism, the gravity-induced hip extension also provides contralateral hip flexion (of the swing leg), such that the stride length of gait is increased. One variation on the RGO incorporates a hydraulic-circuit-based variable coupling between the left and right hip joints. Experiments with this variation indicate improved hip kinematics with the modulated hydraulic coupling.

In order to decrease the high level of exertion associated with passive orthoses, the use of powered orthoses has been previously investigated, which incorporate actuators and an associated power supply to assist with locomotion. More recently, a powered orthosis was developed by combining three electric motors with an RGO, two of which are located at the knee joints to enable knee flexion and extension during swing, and one of which assists the hip coupling, which in essence assists both stance hip extension and contralateral swing hip flexion. The orthosis was shown to increase gait speed and decrease compensatory motions, relative to walking without powered assistance.

In addition, control methods have been proposed for providing assistive maneuvers (sit-to-stand, stand-to-sit, and walking) to paraplegic individuals with the powered lower limb orthosis HAL, which is an emerging commercial device with six electric motors (i.e., powered sagittal plane hip, knee, and ankle joints). Like the powered lower limb orthosis HAL, two additional emerging commercial devices include the ReWalk™ powered orthosis from Argo Medical Technologies and the eLEGS™ powered orthosis from Berkeley Bionics. Both of these devices were developed specifically for use with paraplegic individuals.

SUMMARY

Embodiments of the invention concern a movement assistance device embodied as a powered lower limb orthosis or exoskeleton that, like the devices already mentioned, is intended to provide gait assistance to paraplegics by providing sagittal plane assistive torques at both hip and knee joints. An orthosis in accordance with the various embodiments is different from conventional orthoses in the fact that it neither includes a portion that is worn over the shoulders, nor a portion that is worn under the shoes. Also, an orthosis in accordance with the various embodiments has a significantly lower mass relative to the respective masses reported for other devices.

Additionally, orthoses in accordance with the various embodiments includes a new control architecture that enables a user to intuitively and autonomously control (i.e., without push-button controls or the assistance of a system operator) the basic movements associated with legged mobility (i.e., sitting, standing, and walking). In particular, a control architecture is provided that enables a user to autonomously navigate through these movements, without the use of buttons or switches or the aid of an external operator. Specifically, the control architecture in accordance with the various embodiments enables the user to switch between sitting, standing, and walking, based on the user's upper body movement and the state of the orthosis.

The control architecture of the various embodiments also does not require any instrumentation under the foot, such as ground contact sensors or ground load sensors. Specifically, the controller architecture strictly requires measurement of eight angles, all easily measurable by the lower limb exoskeleton. Based on these eight angles, the control method enables the user to intuitively and autonomously control (i.e., without push-button controls, without the assistance of a system operator, and without instrumentation on the torso, arms, stability aid, or under the feet) the basic movements associated with legged mobility (i.e., sitting, standing, walking, stopping, stair ascent and descent). In some embodiments, the control architecture can also function using a subset of these eight angles.

A powered limb prosthesis in accordance with the various embodiments can be supplemented with functional electrical stimulation (FES) of the user's muscles (i.e., using electrical stimulation to elicit contractions of the user's muscles). The FES can be controlled to provide as much movement as possible, with the remaining movement provided by the assistance device.

DETAILED DESCRIPTION

Figure 1:
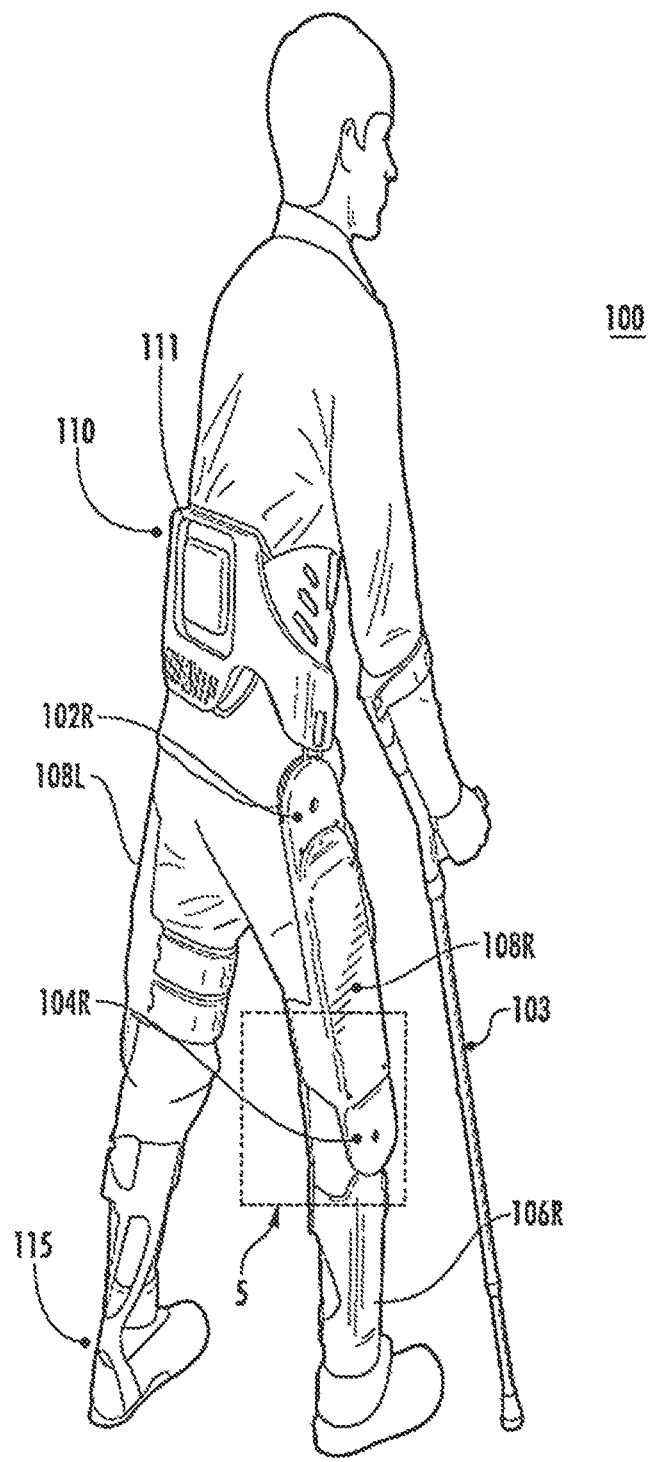
FIG. 1 illustrates a user using an orthosis in accordance with the various embodiments.
Figure 2:
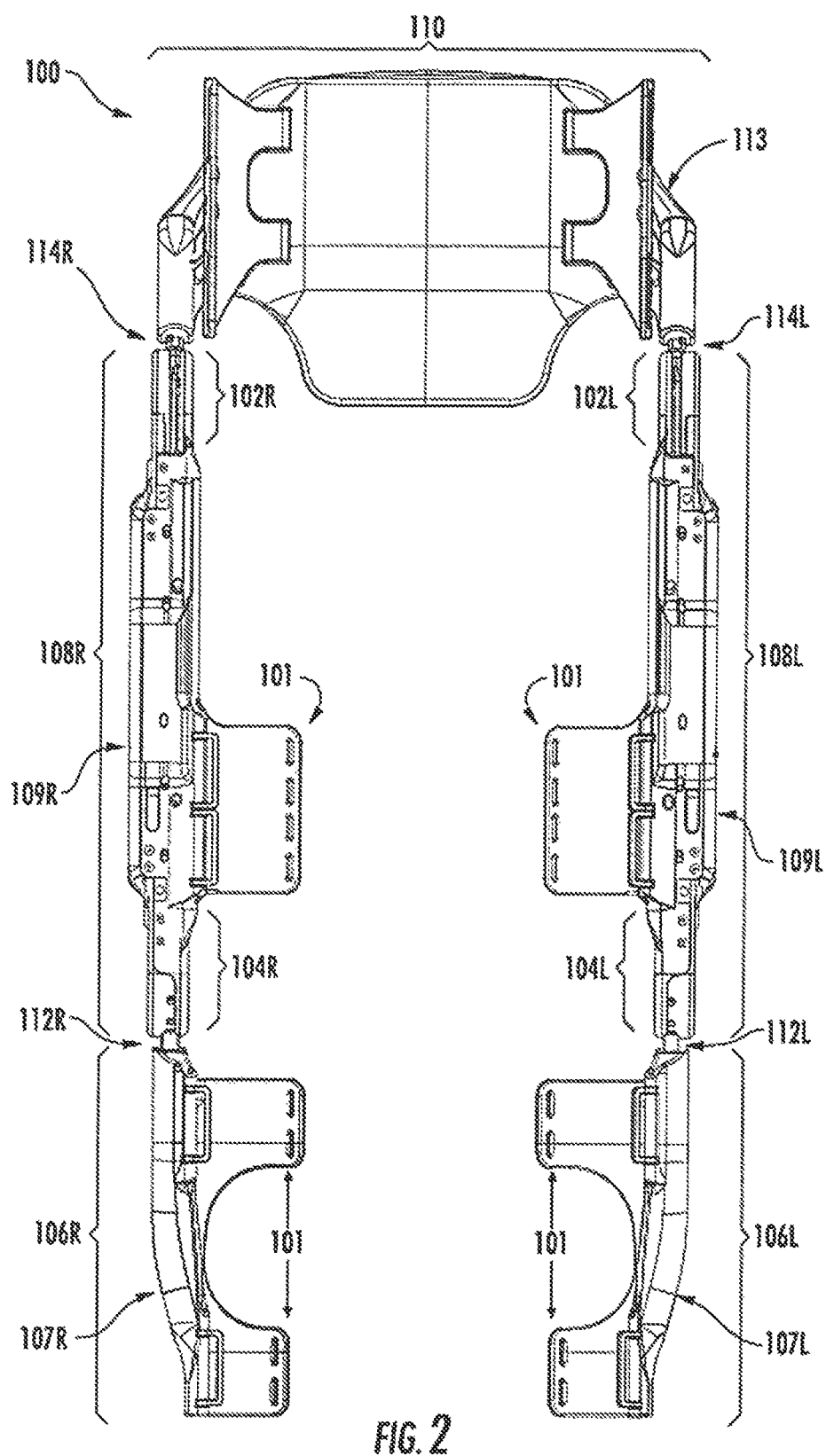
FIG. 2 shows a front view of the orthosis shown in FIG. 1.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

1. POWERED ORTHOSIS CONFIGURATION

Although the various embodiments will be discussed at times with respect to orthoses for providing mobility assistance for users with paraplegia, the various embodiments are not limited in this regard. The various embodiments are equally application to other applications. For example, these can include mobility assistance for users with other conditions other than paraplegia, rehabilitation and mobility assistance for stroke-impaired users, and mobility assistance for users with neuromuscular disabilities that impair legged mobility, to name a few, including human and non-human users. Thus, the various embodiments can be applied to any applications in which mobility assistance or enhancement is needed, either permanently or temporarily.

Further, although the various embodiments will be generally described with respect to the exemplary orthosis described below, the various embodiments are not limited to this particular configuration. The various embodiments can be embodied in or used with any type of exoskeleton system, such as the orthosis described below.

The term "exoskeleton system", as used herein, refers to any type of device that can be worn or otherwise attached to a user, where the device is configured to provide energy for motion of the one or more portions of the user.

An exemplary powered lower limb orthosis 100 in accordance with the various embodiments is shown in FIGS. 1-4.

Specifically, the orthosis 100 shown in FIGS. 1-4 incorporates four motors, which impose sagittal plane torques at each hip joint 102R, 102L and knee joint 104R, 104L. The orthosis 100 can be used with a stability aid 103, such as crutches, a walker, or the like.

As seen in the figure, the orthosis contains five segments, which are: two shank segments 106R and 106L, two thigh segments 108R and 108L, and one hip segment 110. Each of thigh segments 108R and 108L includes a thigh segment housing 109R and 109L, respectively, and link or connector 112R and 112L, respectively, extending from each of the knee joints 104R and 104L and configured for moving in accordance with the operation of the knee joints 104R and 104L to provide sagittal plane torque at the knee joints 104R and 104L. The connectors 112R and 112L are further configured for mechanically coupling each of thigh segments 108R and 108L to respective ones of the shank segments 106R and 106L. Further, each of thigh segments 108R and 108L also includes a link or connector 114R and 114L, respectively, extending from each of the hip joints 102R and 102L and moving accordance with the operation of the hip joints 102R and 102L to provide sagittal plane torque at the knee joints 104R and 104L. The connectors 114R and 114L are further configured for mechanically coupling each of thigh segments 108R and 108L to the hip segment 110.

As show in FIG. 1, the orthosis 100 can be worn by a user. To attach the orthosis to the user, the orthosis 100 can include fastening points 101 for attachment of the orthosis to the user via belts, loops, straps, or the like. Further, for comfort of the user, the orthosis 100 can include padding (not shown) disposed along any surface likely to come into contact with the user.

In some embodiments, the various components of orthosis 100 can be dimensioned for the user. However, in other embodiments, the component can be configured to accommodate a variety of users. For example, in some embodiments, one or more extension elements can be disposed between the shank segments 106R and 106L and the thigh segments 108R and 108L to accommodate users with longer limbs. In other configurations, the lengths of the two shank segments 106R and 106L, two thigh segments 108R and 108L, and one hip segment 110 can be adjustable. That is, thigh segment housings 109R, 109L, the shank segment housings 107R and 107L for the shank segments 106R, 106L, respectively, and the hip segment housing 113 for the hip segment 110 can be configured to allow the user or prosthestist to adjust the length of these components in the field. For example, these components can consist of slidable or movable sections that can be held in one or more positions using screws, clips, or any other types of fasteners. In view of the foregoing, the two shank segments 106R and 106L, two thigh segments 108R and 108L, and one hip segment 110 can form a modular system allowing for one or more of the components of the orthosis 100 to be selectively replaced and for allowing an orthosis to be created for a user without requiring customized components. Such modularity can also greatly facilitate the procedure for donning and doffing the device.

In orthosis 100, disposed within each of thigh segment housings 109R, 109L includes substantially all the components for operating corresponding ones of the knee joints 104R, 104L and the hip joints 102R, 102L. In particular, each of thigh segment housings 109R, 109L includes two motors which are used to drive the hip and knee articulations. However, the various embodiments are not limited in this regard and some components can be located in the hip segment 110 and/or the shank segments 106R, 106L. For example, a battery 111 for the orthosis can be located within in hip segment housing 113 and connectors 114R and 114L can also provide means for connecting the battery 111 to any components within either of thigh segments 108R and 108L. For example, the connectors 114R and 114L can include wires, contacts, or any other types of electrical elements for electrically connecting battery 111 to electrically powered components in thigh segments 108R and 108L. In the various embodiments, the placement of battery 111 is not limited to being within hip segment housing 113. Rather, the battery can be one or more batteries located within any of the segments of orthosis 100.

Figure 5A:
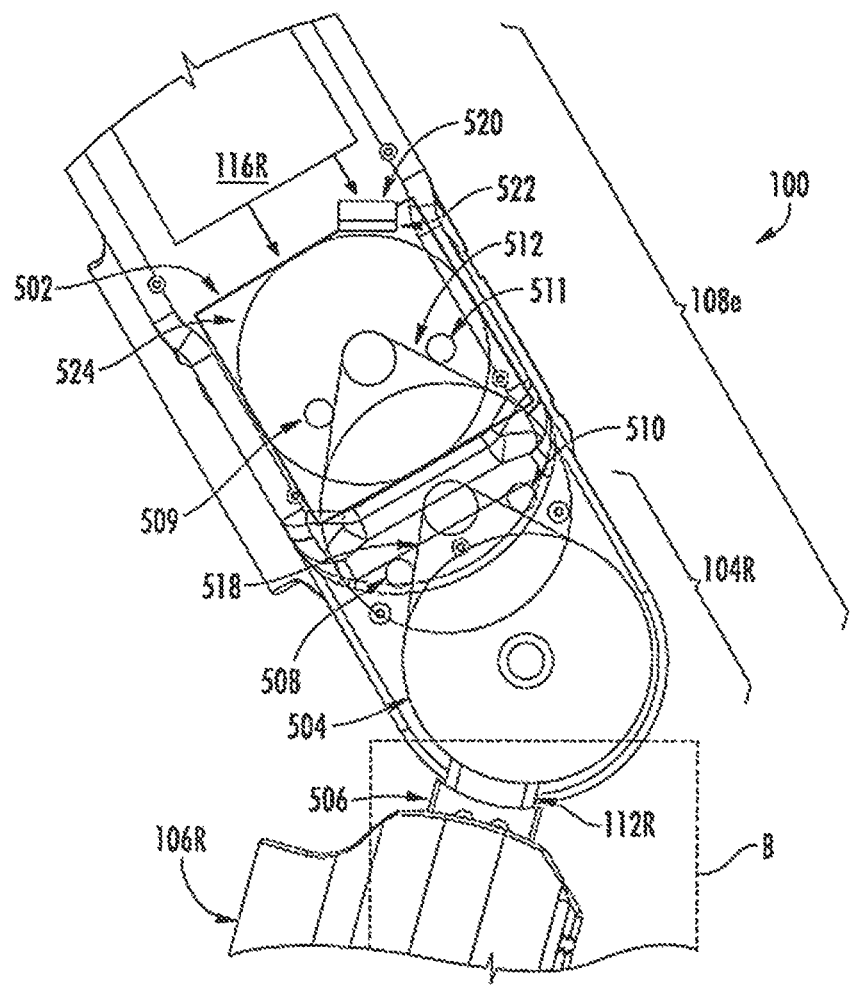
FIG. 5A shows a partial cutaway view of a portion of the orthosis shown in FIG. 1.

In the various embodiments, in order to maintain a low weight for orthosis and a reduced profile for the various components, a substantially planar drive system is used to drive the hip and knee articulations. For example, each motor can each drive an associated joint through a speed-reduction transmission using an arrangement of sprocket gears and chains substantially parallel to the plane of sagittal motion. One exemplary configuration for such an arrangement of a motor is illustrated in FIG. 5A. Using the configuration in FIG. 5A, it is possible to achieve a low profile orthosis, adding less than 5 cm at the hip and thigh sections.

For example, in one embodiment, the profile of the orthosis in the frontal plane can be configured so as to add 3.2 cm at the hip and knee joint, and 4.8 cm at mid-thigh, such that a user is able to sit in a conventional armchair or wheelchair. Similarly, the hip segment protrudes approximately 3.2 cm posteriorly from the user's lower back, such that it should not significantly interfere with a seat back. The orthosis does not extend above mid-abdomen and requires nothing to be worn over the shoulders and nothing above the lower back, which presumably renders the device less noticeable when sitting at a desk or table. The compact design of the orthosis is greatly facilitated by the integration of the distributed embedded system within the orthosis structure.

In the various embodiments, the orthosis 100 is not configured for weight bearing. That is, as shown in FIG. 1, the orthosis 100 will not include feet or other weight bearing structures. Rather, as shown in FIG. 1, the orthosis 100 is configured so that the combined lenth of the shank segments 106R and 106L and the corresponding one of the thigh segments 108R and 108L is less than a length of the leg of the user. This results in an orthosis with potential health benefits for the user. In particular, the ability to stand and walk can reverse or reduce the amount of physiological impairments typically associated with immobility, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities.

Although FIG. 5A will be described with respect to the operation of knee joint 104R, this is for ease of illustration. That is, the other joints can be configured to operate in a substantially similar manner. FIG. 5A is a cutaway view of orthosis 100 around knee joint 104R illustrating one exemplary configuration for a motor 502 driving knee joint 102R in an orthosis in accordance with the various embodiments. As shown in FIG. 5A, the knee joint 102R can be implemented by disposing a joint sprocket gear 504 at one end of thigh segment housing 109R parallel to the sagittal plane and configuring the joint sprocket gear 504 to rotate parallel to the sagittal plane. To provide the sagittal plane torque for knee joint 102R, the connector 112R can extend from the joint sprocket gear 504 and be mechanically connected, so that rotation of the joint sprocket gear 504 results application of torque to the shank segment 106. As shown in FIG. 5A, a slot or receiving element 506 can be provided for the connector 112R to link the thigh segment 108R and shank segment 106R. The receiving element 506 and the connector 112R can be configured such that the connector can removably connect the thigh segment 108R and shank segment 106R. In the various embodiments, clips, screws, or any other types of fastener arrangements can be used to provide a permanent or a removable connection. In some embodiments, quick connect or "snap-in" devices can be provided for providing the connection. That is, these quick connect devices allow connections to be made without the need of tools. These types of quick connect devices can not only be used for mechanically coupling, but for electrical coupling. In some embodiments, a single quick connect device can be used to provide both electrical and mechanical coupling. However, the various embodiments are not limited in this regard and separate quick connect devices can be provided for the electrical and mechanical coupling. It is worth noting that with quick disconnect devices at each joint, the orthosis can be easily separated into three modular components—right leg, left leg, and hip segment—for ease of donning and doffing and also for increased portability.

Figure 5B:
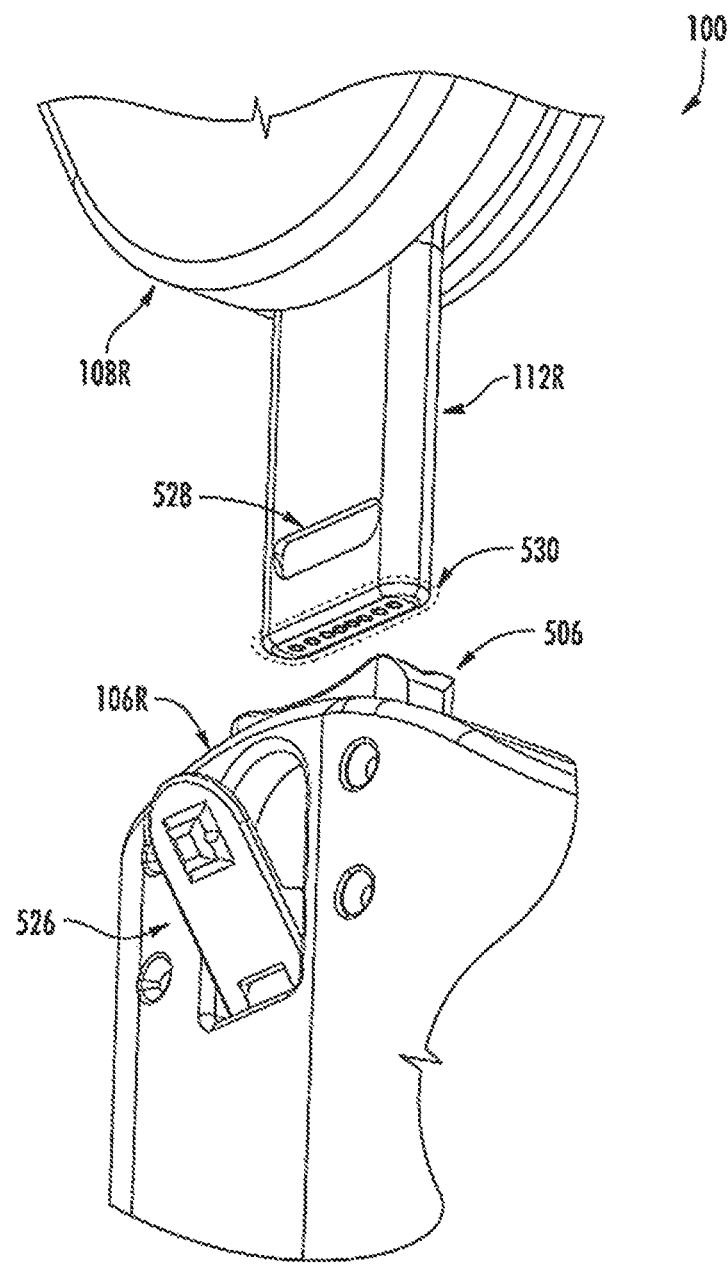
FIG. 5B is a detailed exploded view of section B of FIG. 5A.

A detailed view of an exemplary quick-connect configuration is shown in FIG. 5B. FIG. 5B is a detailed view of section "B" of FIG. 5A. As shown in FIG. 5B, the connector 112R is a member that extends from thigh segment 108R. The connector 112R is configured to slide into receiving element 506. The connector 112R can then be mechanically locked into place via the combination of a latch 526 on shank segment 106R and a catch 528 on connector 112R.

As noted above, the connectors 112R, 112L, 114R, and 114L can be configured to provide mechanical and electrical connections. Referring back to FIG. 5B, in the event that an electrical connection is needed between the thigh segment 108R and shank segment 106R, wires can be routed through the interior of connector 112R to electrical contacts 530. A corresponding set of electrical contacts (not shown) would also be provided in the interior of receiving element 506. Accordingly, when connector 112R is locked into receiving element 506, the electrical contacts 530 are placed in contact with the electrical contacts within receiving element 506. A similar configuration can be provided for links 112L, 114R, and 114L. It is noted though that the various embodiments are not limited to solely the catch and latch combination of FIG. 5B. Rather any other type of fastening or locking mechanism can be used without limitation.

Referring back to FIG. 5A, the knee joint 104R is actuated via operation of motor 502, as discussed above. The motor 502 can be an electric motor that drives the knee joint 104R (i.e., joint sprocket gear 504) using a two-stage chain drive transmission. For example, as shown in FIG. 5A, a first stage can consist of the motor 502 driving, either directly or via a first chain 512, a first drive sprocket gear 514. The first drive sprocket gear 514 is mechanically coupled to a second drive sprocket gear 516 so that they rotate together about the same axis based on the power applied by motor 502 to first drive sprocket gear 514. The second drive sprocket gear 516 can be arranged so that it is disposed in the same plane as the joint gear 504. Thus, a second chain 518 can then be used to drive joint sprocket gear 504 using the second drive sprocket gear 516 and actuate the knee joint 104R. The gear ratios for the various components described above can be selected based on a needed amount of torque for a joint, power constraints, and space constraints.

Each stage of the chain drive transmission can include tensioners, which can remove slack from a chain and mitigate shock loading. Such tensioners can be adjustable or spring loaded. For example, as shown in FIG. 5A, spring loaded tensioners 508 and 510 are shown for second chain 518. Similarly, tensioners 509 and 511 can also be provided for first chain 512 (if present).

In addition, a brake can be provided for motor 502. For example, as shown in FIG. 5, a solenoid brake 520 is provided which engages a brake pad 522 against the rotor 524 of the motor 502 in one state, and disengages the brake pad 522 in another state. However, the various embodiments are not limited to this particular brake arrangement and any other methods for providing a brake for motor 502 can be used without limitation.

The configuration illustrated in FIG. 5A has been discussed above with respect to an arrangement of sprocket gears and chains. However, the various embodiments are not limited in this regard. That is, any other arrangement of gears, with or without chains, and providing a reduced profile can be used. Further, the various embodiments are not limited to an arrangement of gears and/or chains For example, in some configurations, a belt and pulley arrangement could be used in place of the chain and sprocket arrangement. Further, a friction drive arrangement can also be used. Also, any combination of the arrangements discussed above can be used as well. Additionally, different joints can employ different arrangements.

In the various embodiments, a motor for each of joints 102R, 102L, 104R, 104L can be configured to provide a baseline amount of continuous torque and a higher amount of torque for shorter periods of time. For example, in one configuration, at least 10 Nm of continuous torque and at least 25 Nm of torque for shorter (i.e., 2-sec) durations are provided. In another example, up to 12 Nm of continuous torque and 40 Nm of torque for shorter (i.e., 2-sec) durations. As a safety measure, both knee joints 104R and 104L can include normally locked brakes, as discussed above, in order to preclude knee buckling in the event of a power failure.

It is worth noting that an orthosis in accordance with the various embodiments does not contain foot or ankle components. However, an orthosis in accordance with the various embodiments can be configured to be used in conjunction with a standard ankle foot orthosis (AFO) 115 to provide stability for the ankle and/or to preclude foot drop during the swing phase of gait.

Figure 3:
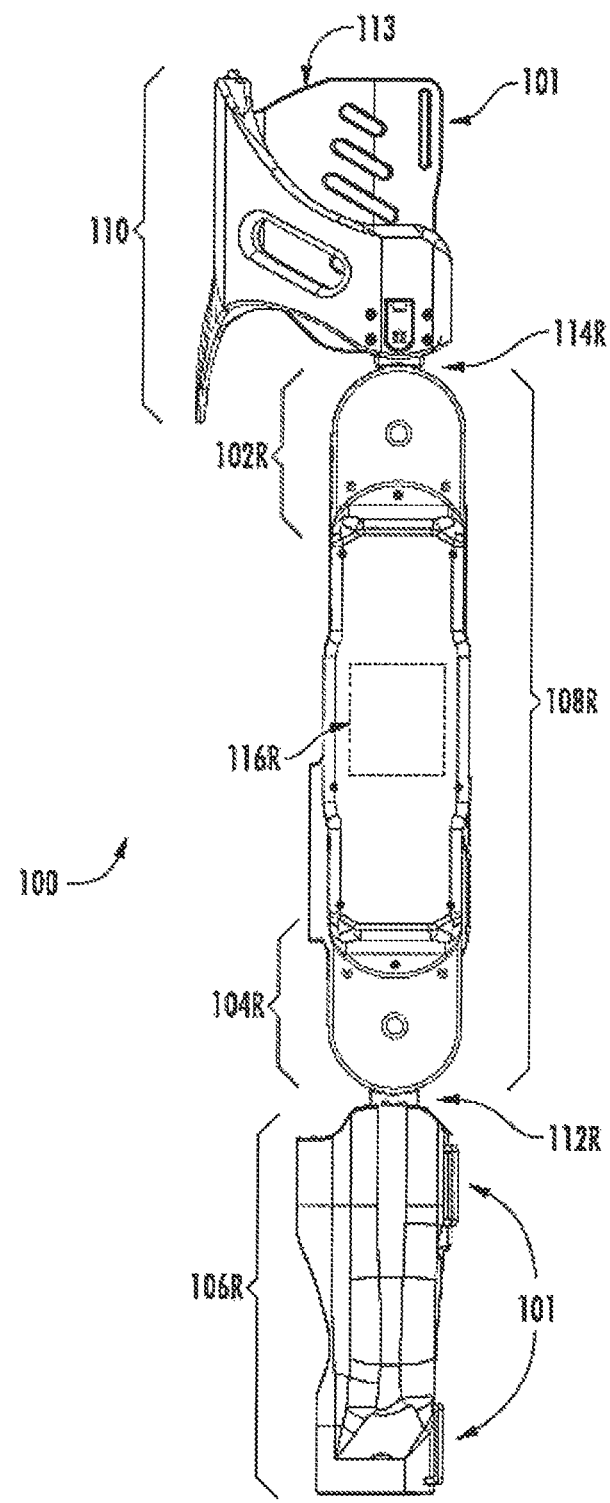
FIG. 3 shows a side view of the orthosis shown in FIG. 1.
Figure 4:
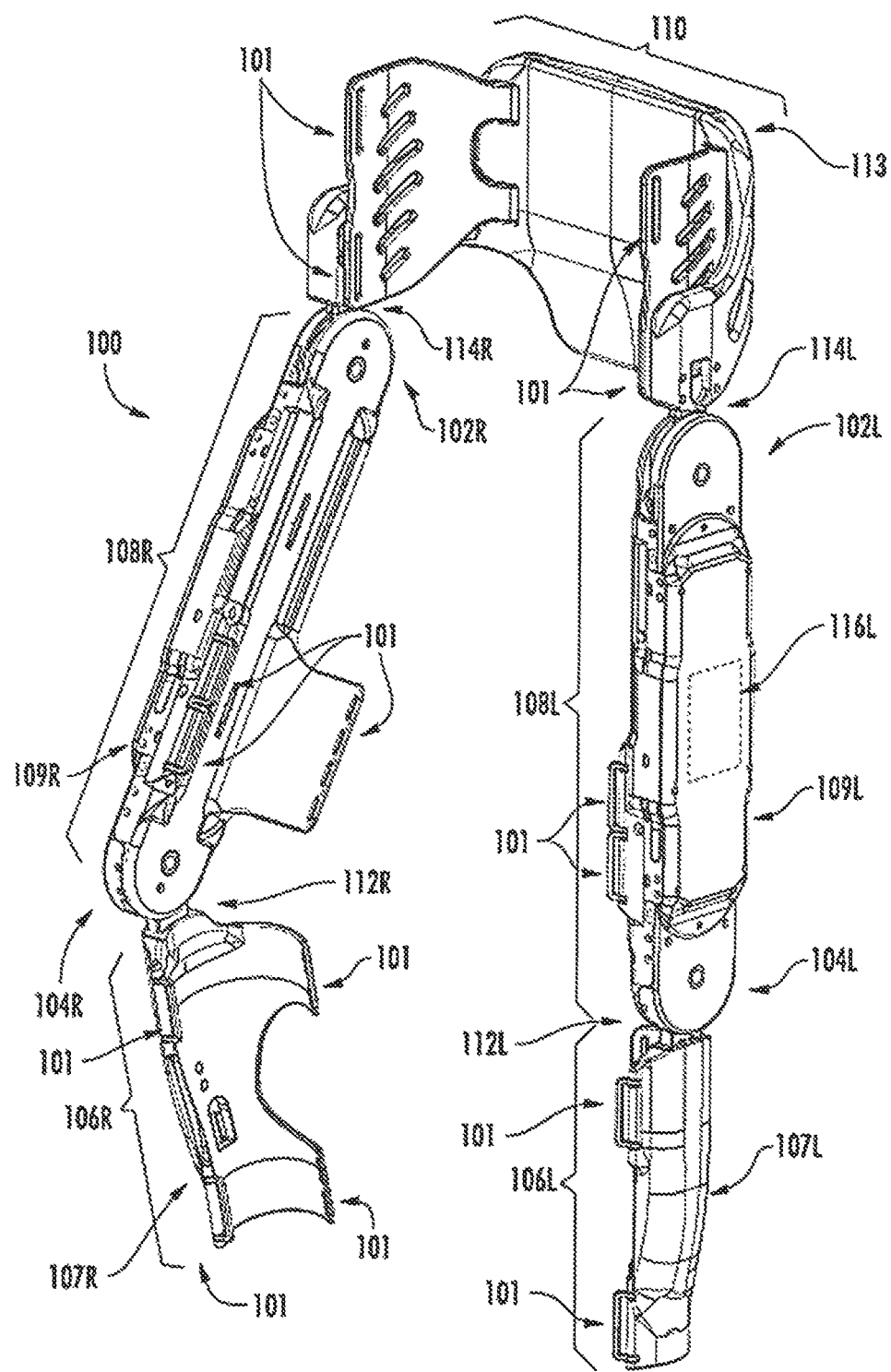
FIG. 4 shows an isometric view of the orthosis shown in FIG. 1.

In the orthosis 100, control of the various joints is provided using a pair of embedded control systems 116R and 116L embedded in one of thigh segments 108R and 108L, respectively. The embedded control systems 116R and 116L can be used to define a distributed embedded system (DES) to provide cooperative operation between thigh segments 108R and 108L. The embedded control systems 116R and 116L are shown in FIGS. 3 and 4 using dashed lines to indicate they are concealed by other features in these figures.

Figure 6:
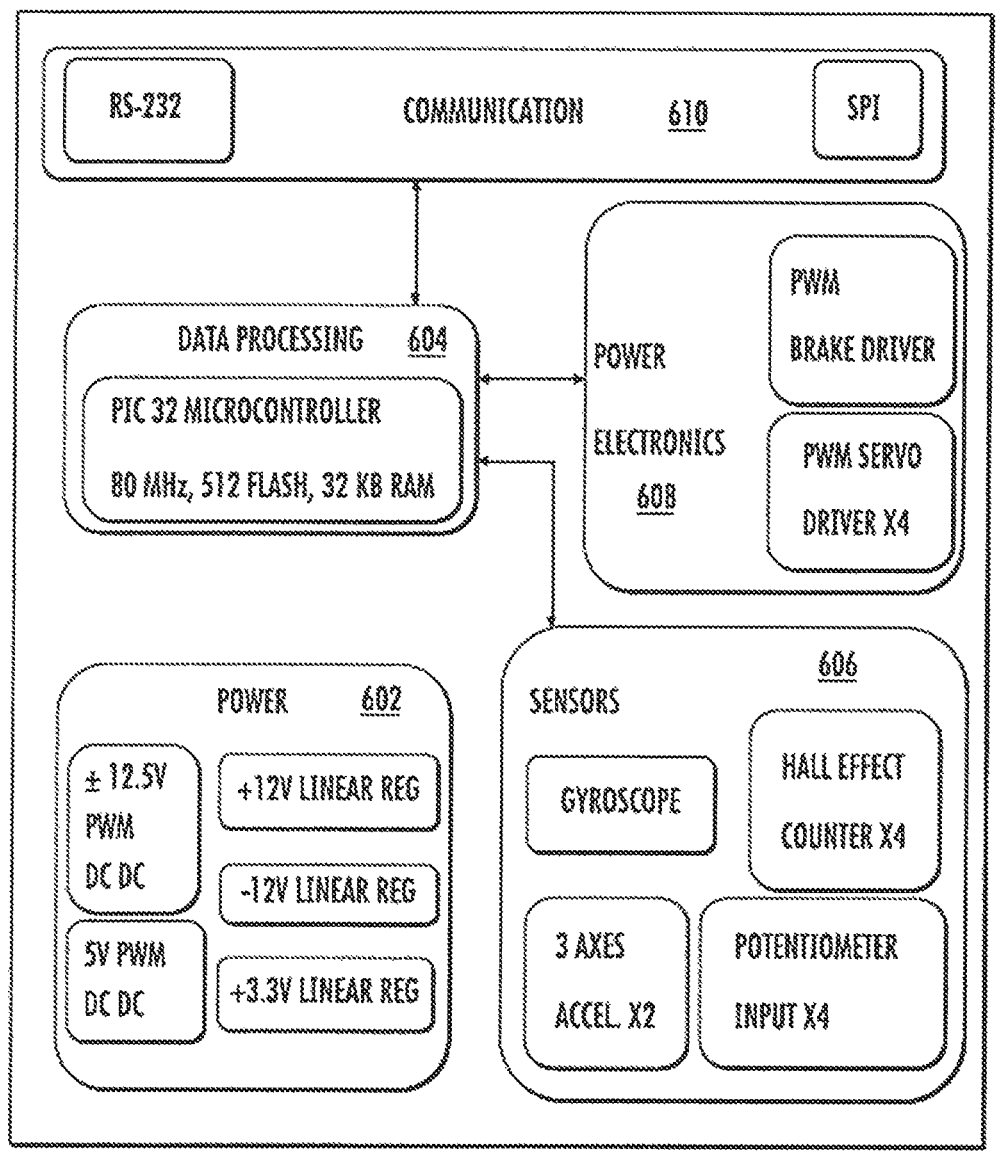
FIG. 6 is a functional diagram of an exemplary distributed embedded system for an orthosis in accordance with the various embodiments.

A functional diagram of an exemplary DES 600 formed using the embedded control systems 116R and 116L is given in FIG. 6. The DES 600 is powered by battery 111, such as a 29.6 V, 3.9 A·hr lithium polymer battery. The DES 600 can include includes a power management module 602, a computation or data processing module 604, electronic signal conditioning and sensor interface module 606, power electronics 608, and communication electronics 610 to interface components within the DES 600 and between the DES 600 and a host computer. To form the DES 600 the embedded control systems 116R and 116L can be communicatively coupled via wired communications links in the hip segment 110 or wireless communications links between the embedded control systems 116R and 116L. The can include any type of wireless communications links. For example, these can include wireless communication links according to any of the IEEE 802.xx standards, Bluetooth™, and any derivations thereof. However, the various embodiments are not limited in this regard and any other types of wireless communication links can be used.

The power management module 602 provides, from the battery 111 can provide signal conditioning and regulation. Additionally, the power management modules For example, the power management module 602 is configured to provide linearly regulated ±12 and +3.3 V, which are used for signal conditioning and computation, and are derived from intermediate ±12.5 and +5 V switching regulators for efficient conversion. In some embodiments, the orthosis 100 can include a visual display, controlled by the power management module 602, to indicate a state of the battery. The visual display can be alphanumeric or symbolic (e.g., one or more lights to indicate battery status).

The computation module 604 consists of microcontroller units within each of embedded control systems 116R and 116L. For example, as shown in FIG. 6, the microcontroller units can be s 80 MHz PIC32 microcontrollers, each with 512 kB flash memory and 32 kB RAM, and each of which consume approximately 400 mW of power. These microcontrollers can be programmed. For example, the programming can be performed in C programming language using MPLAB IDE and the MP32 C Compiler (both from Microchip Technology, Inc.). However, the various embodiments are not limited in this regard and any other types of programming methods can be used.

In operation, the computation module 604 (i.e., the two microcontrollers) drive the motors associated with each of joints 102R, 102L, 104R, and 104L using servodrivers or servoamplifiers in the power electronics 608, such as four-quadrant switching servoamplifiers or pulse-width-modulated (PWM) power transistor drivers. The computation module 604 also drives the knee brakes via pulse-width-modulated (PWM) power transistors in the power electronics 608.

The computation module 604 is configured in the various embodiments to drive the motors associated with each of joints 102R, 102L, 104R, and 104L based, at least in part, on sensor data regarding the state of the orthosis 100, as further discussed below. Accordingly, the sensor interface module 606 can be configured to provide and/or provide communications with sensors dispose in orthosis 100. In some embodiments, all of the sensors can be disposed within one of thigh segments 108R and 108L. For example, these sensors can be embedded within each of embedded control systems 116R and 116L. In one configuration of orthosis 100, physical sensing consists of Hall-effect-based angle and angular velocity sensing in each hip joint 104R, 104L and each knee joint 102R, 102L, and 3-axis accelerometers and single-axis gyroscopes disposed elsewhere in each of thigh segments 108R and 108L.

Although the description above describes a symmetric arrangement of components in for each of embedded control systems 116R and 116L, the various embodiments are not limited in this regard. In other embodiments, one or more of the module described above may be located within one of embedded control systems 116R and 116L.

In some embodiments, the orthosis 100 can be configured to operate cooperatively with sensors embedded in the stability aid 103. The DES can be configured to communicate with such sensors via wireline or wireless communications links, as described above.

2. POWERED ORTHOSIS CONTROL ARCHITECTURE

2.1 Joint-Level Controllers

The general control structure of an orthosis in accordance with the various embodiments consists of variable-impedance joint-level controllers, the behavior of which is supervised by an event-driven finite-state controller. The joint-level controllers consist of variable-gain proportional-derivate (PD) feedback controllers around each (hip and knee) joint, where at any given time, the control inputs into each controller consists of the joint angle reference, in addition to the proportional and derivative gains of the feedback controller. Note that the latter are constrained to positive values, in order to ensure stability of the feedback controllers. With this control structure, in combination with the open-loop low output impedance of the orthosis joints, the joints can either be controlled in a high-impedance trajectory tracking mode, or in a (relatively) low-impedance mode, by emulating physical spring-damper couples at each joint. The former is used where it may be desirable to enforce a predetermined trajectory (e.g., during the swing phase of gait), while the latter is used when it may be preferable not to enforce a pre-determined joint trajectory, but rather to provide assistive torques that facilitate movement toward a given joint equilibrium point (as in transitioning from sitting to standing), or to impose dissipative behavior at the joint (as in transitioning from standing to sitting).

2.2 Finite-State Control Structure

The following section describes one exemplary embodiment of a control structure that enables the autonomous control of standing, walking, and sitting. However, this particular control structure is provided solely for ease of illustration of the various embodiments. In the various embodiments, the control structure can include additional activity modes, which would be implemented in a similar manner. These can include upslope and downslope walking, stair ascent and descent, and curb ascent and descent, to name a few. It is worth noting that curb ascent and descent can also be a subset of the stair ascent and descent functionality.

Figure 7:
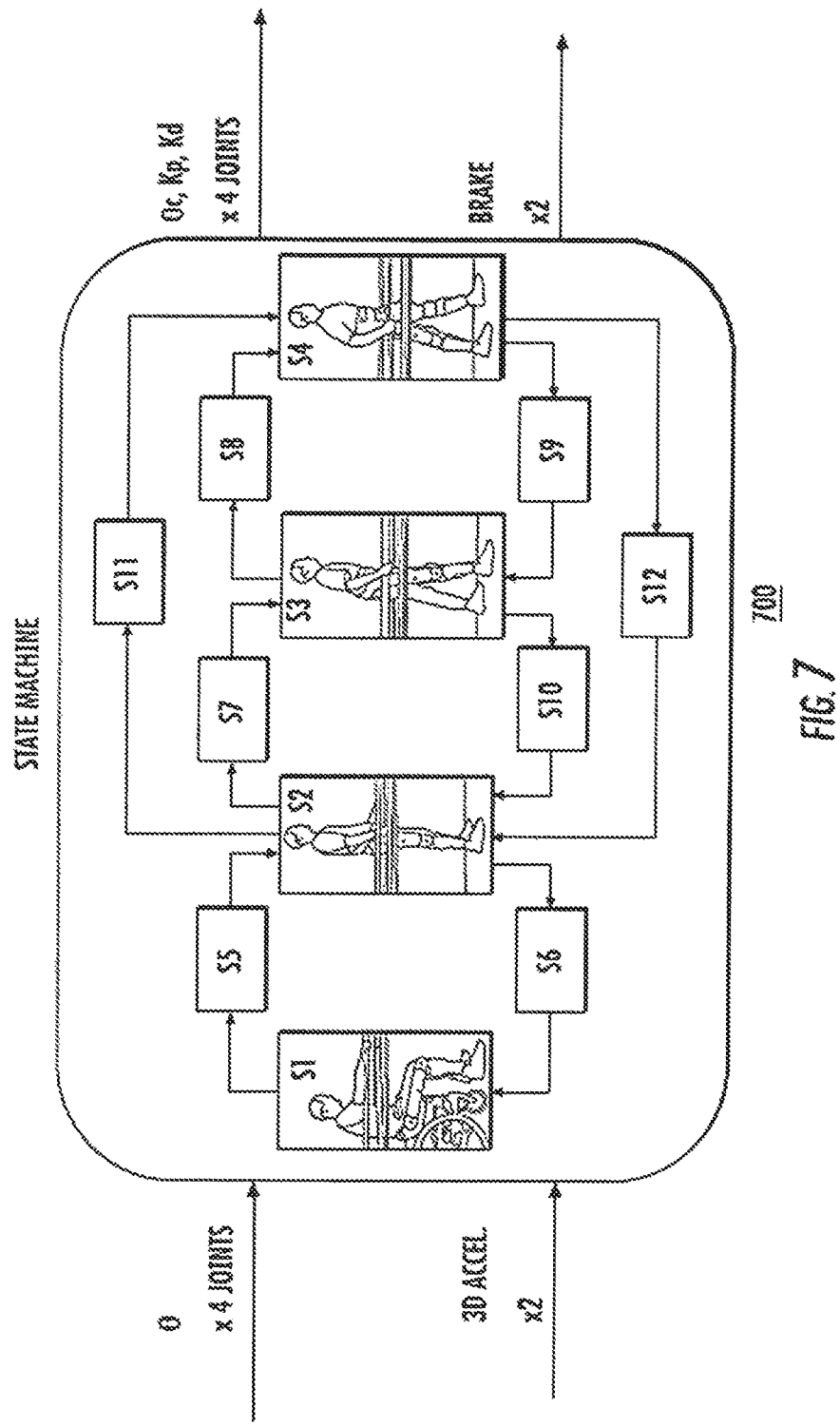
FIG. 7 shows a state machine in accordance with the various embodiments of the invention.

The joint-level controller receives trajectory commands, as well as PD gains, from a supervisory finite-state machine (FSM) 700, which (for sitting, standing, and walking) consists of 12 states, as shown in FIG. 7. The FSM 700 consists of two types of states: static states and transition states. The static states consist of sitting (S1), standing (S2), right-leg-forward (RLF) double support (S3), and left-leg-forward (LLF) double support (S4). The remaining 8 states, which transition between the four static states, include sit-to-stand (S5), stand-to-sit (S6), stand-to-walk with right half step (S7), stand-to-walk with left half step (S11), walk-to-stand with left half step (S10), walk-to-stand with right half step (S12), right step (S9), and left step (S8).

Figure 8A:
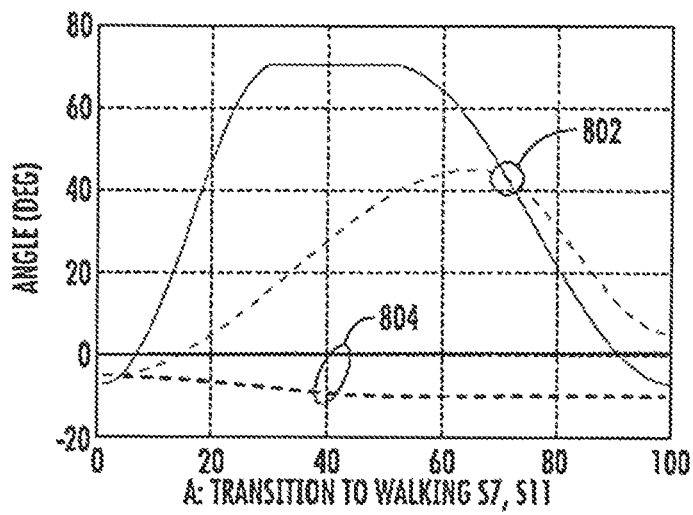
FIG. 8A is an X-Y plot of joint angle a function of the percent of stride during a transition to a walking state.
Figure 8B:
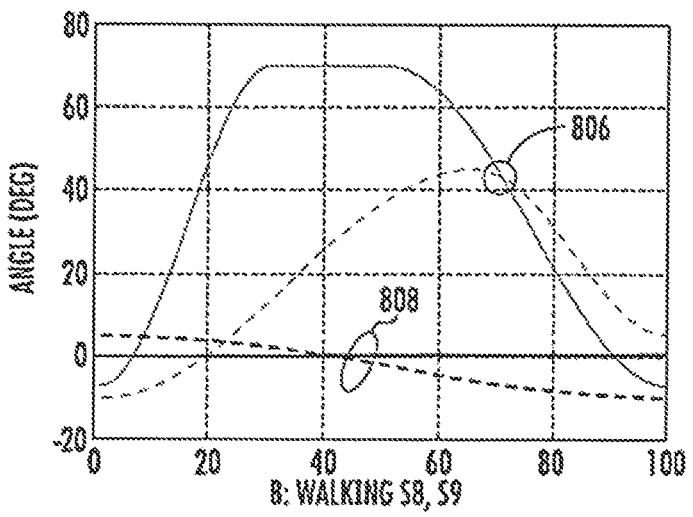
FIG. 8B is an X-Y plot of joint angle a function of the percent of stride during a transition between walking states.
Figure 8C:
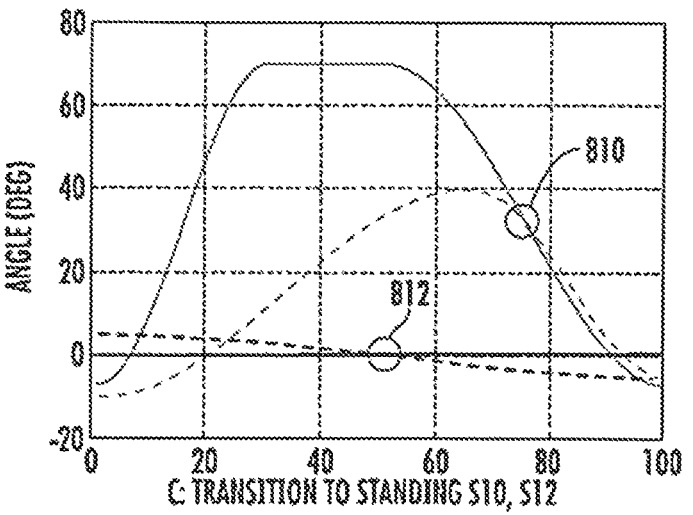
FIG. 8C is an X-Y plot of joint angle a function of the percent of stride during a transition to a standing state.

Each state in the FSM 700 is fully defined by the combination of a set of trajectories, and a set of joint feedback gains. In general, the latter are either high or low. The set of trajectories utilized in six of the eight transition states are shown in FIGS. 8A-8C. FIG. 8A is an X-Y plot of joint angle a function of the percent of stride during a transition to a walking state (S7, S11 in FIG. 7). Curves 802 are curves for swing of the hip and knee, represented by dashed and solid lines, respectively. Curves 804 are curves for stance of the hip and knee, represented by dashed and solid lines, respectively. FIG. 8B is an X-Y plot of joint angle a function of the percent of stride during a transition between walking states (S8, S9 in FIG. 7). Curves 806 are curves for swing of the hip and knee, represented by dashed and solid lines, respectively. Curves 808 are curves for stance of the hip and knee, represented by dashed and solid lines, respectively. FIG. 8C is an X-Y plot of joint angle a function of the percent of stride during a transition to a standing state (S10, S12 in FIG. 7). Curves 810 are curves for swing of the hip and knee, represented by dashed and solid lines, respectively. Curves 812 are curves for stance of the hip and knee, represented by dashed and solid lines, respectively.

For all the trajectories shown in FIGS. 8A-8C, the joint feedback gains are set high. The final angles of the trajectories shown in FIGS. 8A-8C for the various joints define the constant joint angles that correspond to the static states of RLF double support (S3), LLF double support (S4), and standing (S2). Three states remain, which are the static state of sitting (S1) and the two transition states of sit-to-stand (S5) and stand-to-sit (S6). The static state of sitting (S1) is defined by zero gains, and therefore the joint angles are unimportant. The transition from stand-to-sit (S6) consists of a zero proportional gain and a high derivate gain (i.e., damping without stiffness). Thus, the joint angles are also immaterial for this state, assuming they are constant. Finally, the sit-to-stand (S5) state is defined by standing (S2) joint angles, and utilizes a set of PD gains that ramp up from zero to a value that corresponds to a high impedance state. Together, Table I and FIGS. 8A-8C summarize the trajectories and nature of the feedback gains that together define completely the behavior in all states of the FSM shown in FIG. 7.

TABLE 1

Joint controller characteristics within each state.

| State | Type | Gains | Control Priority |
|---|---|---|---|
| S1- Sitting | Static | Low | NA |
| S2- Standing | Static | High | Position |
| S3- Right Forward | Static | High | Position |
| S4- Left Forward | Static | High | Position |
| S5- 1 to 2 | Transition | N.A | Gain |
| S6- 2 to 1 | Transition | N.A | Gain |
| S7- 2 to 3 | Transition | High | Trajectory |
| S8- 3 to 4 | Transition | High | Trajectory |
| S9- 4 to 3 | Transition | High | Trajectory |
| S10- 3 to 2 | Transition | High | Trajectory |
| S11- 2 to 4 | Transition | High | Trajectory |
| S12- 4 to 2 | Transition | High | Trajectory |

2.3 Switching Between States

Figure 9:
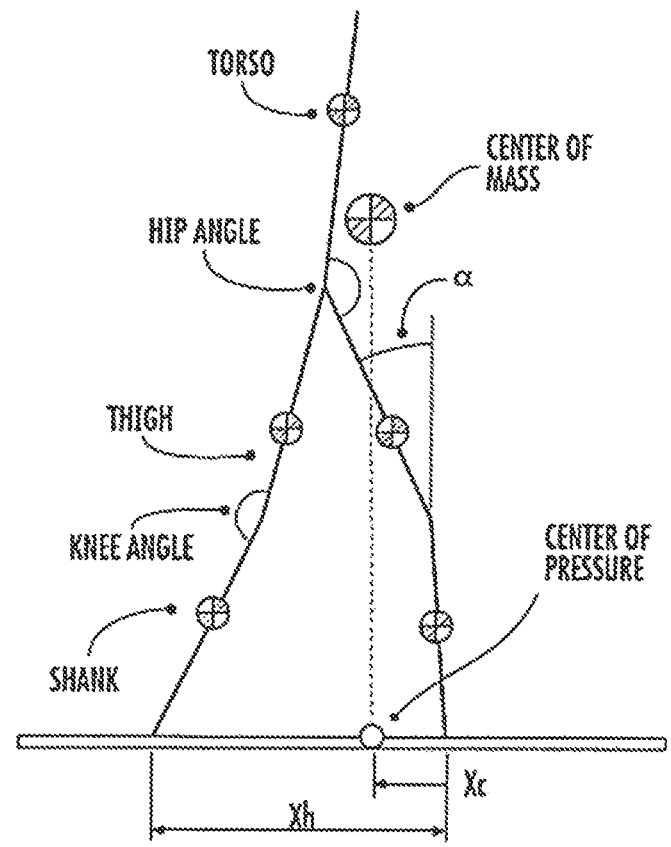
FIG. 9 is a schematic showing center of pressure during walking.

The volitional command of the basic movements in the FSM is based on the location of the (estimated) center of pressure (CoP), defined for the (assumed quasistatic user/orthosis) system as the center of mass projection onto the (assumed horizontal) ground plane. This notion is illustrated in FIG. 9, which is a schematic for illustrating how to determine the approximate location of the CoP, relative to the forward-most heel. It is assumed that, with the use of the stability aid, the user can affect the posture of his or her upper body, and thus can affect the location of the CoP. By utilizing the accelerometers in the orthosis, which provide a measure of the thigh segment angle (a in FIG. 9) relative to the inertial reference frame (i.e., relative to the gravity vector), in combination with the joint angle sensors (which provide a measure of the configuration of the orthosis and user), the orthosis controller can estimate the location of the CoP (in the sagittal plane). More specifically, in this estimation, the authors assume level ground; that the heels remain on the ground; that the head, arms, and trunk (HAT) can be represented as a single segment with fixed inertial properties; and that out-of-sagittal-plane motion is small. Given these assumptions, along with estimates of the length, mass and location of center of mass of each segment (right and left shank, right and left thigh, and HAT), the controller can estimate the projection of the CoP on the ground. Let the distance from the forward-most heel to the CoP be $X_c$, where a positive value indicates that the CoP lies anterior to the heel, and a negative number indicates the CoP lies posterior to the heel (see FIG. 9).

From a state of double support (S3 or S4), the user commands the next step by moving the CoP forward, until it meets a prescribed threshold, at which point the FSM will enter either the right step or left step states, depending on which foot started forward.

From a standing position (S2), the user commands a step by similarly moving the CoP forward until it meets a prescribed threshold, but also leaning to one side in the frontal plane (as indicated by the 3-axis accelerometers in the thigh segments), which indicates that the orthosis should step with the leg opposite the direction of frontal plane lean (i.e., step forward with the presumably unweighted leg). That is, leaning to the right (and moving the CoP forward) will initiate a left step, while leaning to the left (and moving the CoP forward) will initiate a right step.

Figure 10A:
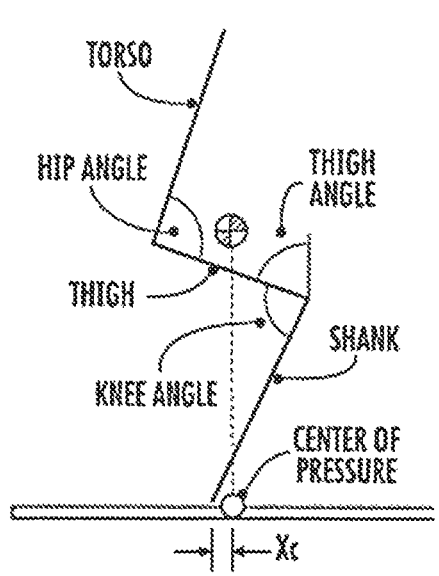
FIG. 10A is a schematic showing center of pressure during a transition from sitting to standing.
Figure 10B:
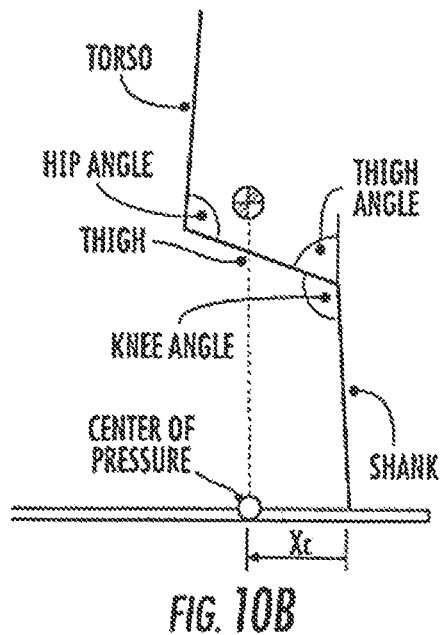
FIG. 10B is a schematic showing center of pressure during a transition from standing to sitting.

The transitions between standing (S2) and sitting (S1) states are illustrated in the schematics show in FIGS. 10A and 10B. To transition from a sitting to a standing state (S1 to S2), the user leans forward as illustrated in FIG. 10A, which shifts the CoP forward to a predetermined threshold, which initiates the transition from sitting to standing. Note that FIG. 10A shows the case where the user's CoP is not sufficiently forward to initiate a transition from sitting to standing. In order to transition from a standing state (S2) to a sitting state (S1), the user shifts the CoP rearward, such that the CoP lies behind the user, as shown in FIG. 10B

Finally the transition from (either case of) double support to standing (i.e., from either S3 or S4, to S2) is based on the timing associated with crossing the CoP threshold. That is, if the CoP does not cross the CoP threshold within a given time following heel strike (i.e., if the controller remains in either state S3 or S4 for a given duration), subsequent crossing of the CoP threshold will transition to standing (S2) rather than to the corresponding double support configuration. That is, a sufficient pause during gait indicates to the system that the user wishes to stand, rather than continue walking forward. A summary of all switching conditions, governing the user interface with the FSM controller, is given in Table 2.

TABLE 2

Finite state controller switching conditions
STATE MACHINE SWITCHING CONDITIONS

| Transition | Condition |
|---|---|
| S1 to S5 | The user leans forward and pushes up. |
| S5 to S2 | Hip and knee joints meet the Standing (S2) configuration. |
| S2 to S7 | The user leans forward and left. |
| S7 to S3 | Hip and knee joints meet the Right Forward (S3) |

TABLE 2-continued

Finite state controller switching conditions
STATE MACHINE SWITCHING CONDITIONS

| Transition | Condition |
| --- | --- |
| S3 to S8 | configuration.<br>The user leans forward. |
| S8 to S4 | Hip and knee joints meet the Left Forward (S4) configuration. |
| S4 to S9 | The user leans forward. |
| S9 to S3 | Hip and knee joints meet the Right Forward (S3) configuration. |
| S3 to S10 | The user pauses for a predetermined period prior to leaning forward. |
| S10 to S2 | Hip and knee joints meet the Standing (S2) configuration. |
| S2 to S6 | The user leans backward. |
| S6 to S1 | A predetermined time has lapsed. |
| S2 to S11 | The user leans forward and right. |
| S11 to S4 | Hip and knee joints meet the Left Forward (S4) configuration. |
| S4 to S12 | The user pauses for a predetermined period prior to leaning forward. |
| S12 to S2 | Hip and knee joints meet the Standing (S2) configuration. |

The previous discussion indicates that the user-initiated right and left steps occur when the estimated location of the CoP (relative to the forward heel) exceeds a given threshold. The authors have found that this approach provides enhanced robustness when this threshold is a function of the step length. That is, despite high-gain trajectory control in the joints of the orthosis during swing phase, scuffing of the foot on the ground, as occasionally occurs, in combination with compliance in the orthosis structure, can alter the step length during walking. In the case of a small step length, the forward thigh is nearly vertical, and the user is more easily able to move the CoP forward of the forward heel. In the case of a large step length, the forward thigh is forms a larger angle with the vertical, and moving the CoP forward is more difficult. As such, the CoP threshold during walking was constructed as a linear function, where the CoP threshold (i.e., the amount the CoP must lie ahead of the forward heel) decreases with increasing step size.

In the various embodiments, any sensors located within a stability aid can be used to provide additional data for determining COP or a current state within the state machine.

In some embodiments, one or more acoustic transducers can be embedded within one or more portions of the orthosis (such as within either of housings 109R and 109L). In such embodiments, the acoustic transducer can be configured to generate acoustic signals (i.e., vibrations) indicating a change in state. For example, the transducer can be operated to provide specific patterns of vibration or sound for each state or transition. In other embodiments, the motors used to actuate the hip or knee joints can be used as the transducer for emitting sound or vibration. In still other embodiments, visual indicia of the state or transition can be provided. That is, a display or lights can be provided to indicate the state or transition. For example, in embodiments including a display or lights indicating a battery state, the display or lights can also be configured to visually indicate the state or transition. In still other embodiments, audio indicia of the state or transition can be provided. That is, one or more sounds can be provided to indicate the state or transition. In yet other embodiments, tactile indicia of the state or transition can be provided. That is, the orthosis can include devices which adjustable features so that the state or transition can be communicated to the user via touch, The control methodology above has been described with respect to an orthosis including thigh and shank segments for both legs of the user. However, the various embodiments are not limited in this regard. In some embodiments, an orthosis can be configured to assist movement of a first leg of a user and allow the user to move a second, sound leg without assistance. In these embodiments, sensors can be positioned to detect the motion of the sound leg and the DES can then determine control signals for the first leg. For example, the user can wear a covering on the sound leg, such as a garment or a splint, which includes these sensors.

2.4 Exemplary Configuration for the Finite-State Control Structure

The control structure described above can be implemented in a variety of ways. However, for ease of illustration and greater understanding of the various embodiments, an exemplary implementation a control structure in accordance with the various embodiments will now be discussed.

Figure 11:
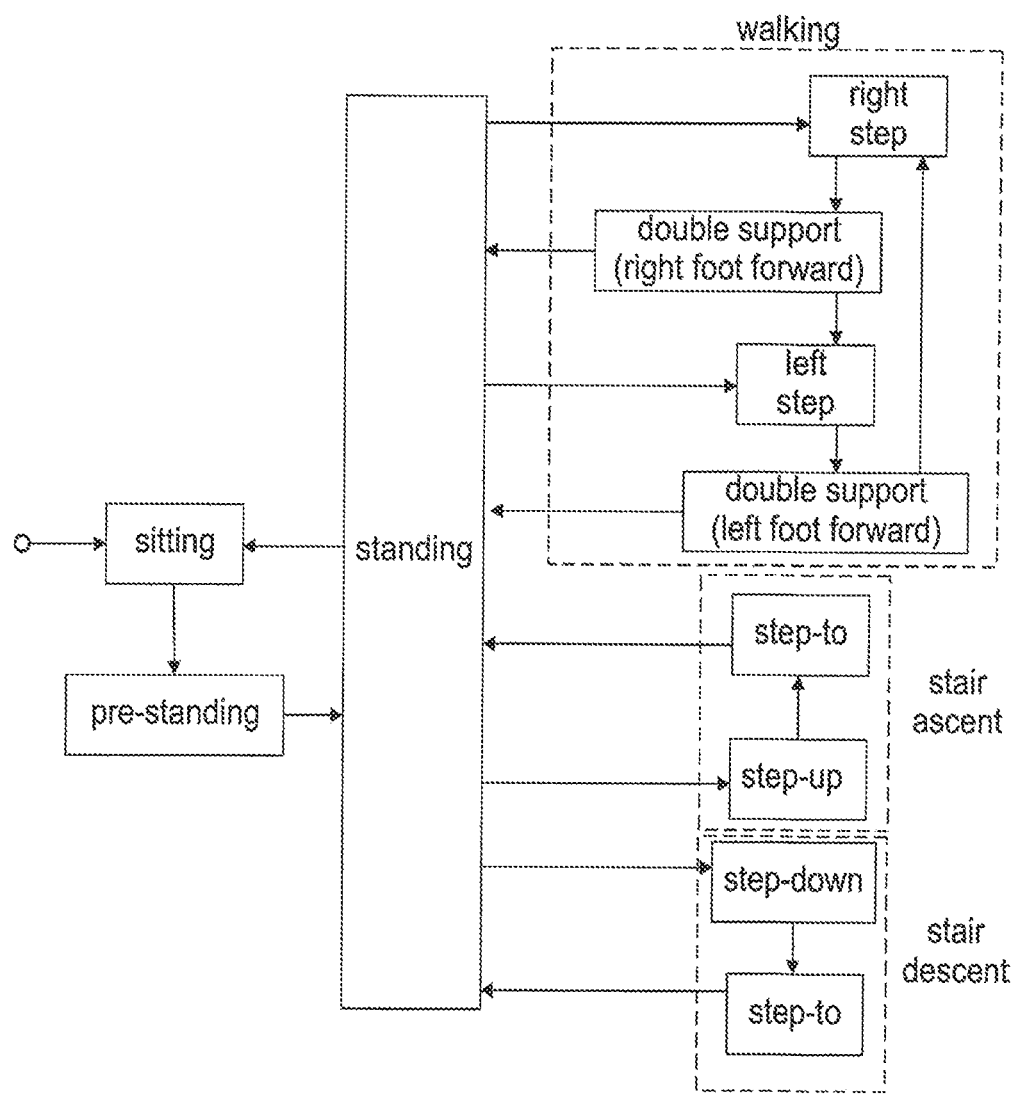
FIG. 11 shows one exemplary structure for a controller in accordance with the various embodiments of the invention.

The exemplary control method incorporates a finite state structure as illustrated in FIG. 11. In particular, the method switches between the states shown in FIG. 11 utilizing measurement of the exoskeleton configuration as defined in FIGS. 12A and 12B. Specifically, measurement of the exoskeleton configuration, as described here, includes measurement of eight angles, which include the knee and hip angles of the exoskeleton (i.e., the angles $\theta_{rh}$, $\theta_{rk}$, $\theta_{lh}$, and $\theta_{lk}$ in FIG. 12A), in addition to measurement of the right and left thigh angles relative to the vertical (i.e., relative to the gravity vector g). The latter includes the angles with respect to the vertical in the sagittal plane (i.e., x-y plane in FIG. 12A) of the left and right thigh segments (the angles $\alpha_r$ and $\alpha_l$ in FIG. 12A), and the angles with respect to the vertical in the frontal plane (i.e., y-z plane in FIG. 12B) of the left and right thigh segments (the angles $\gamma_r$ and $\gamma_l$ in FIG. 12B).

2.4.1 Walking

As depicted in FIG. 11, the exemplary walking controller consists of at least a right stepping motion (right step) and a left stepping motion (left step), generally separated by a double-support phase (both feet on the ground), in which either the right or left foot, respectively, is forward. In the proposed method, the user indicates intent to take the next step (i.e., to trigger a right or left stepping motion) based on the angle with respect to the vertical in the sagittal plane of the forward thigh (i.e., $\alpha$ of the forward leg) exceeding a predetermined threshold (where moving the forward thigh in the clockwise direction, as shown in the figure, will trigger a subsequent step of the opposite leg). This can be referred to as "thigh tilt" in the sagittal plane. The user can affect the thigh tilt via use of his or her stability aid (e.g., forearm crutches or walker). The step triggering threshold can further be a function of the size of the previous step, as indicated for example by the difference between the right and left hip angles in the double support phase, or the difference between the right and left thigh angles.

Figures 12A, 12B:
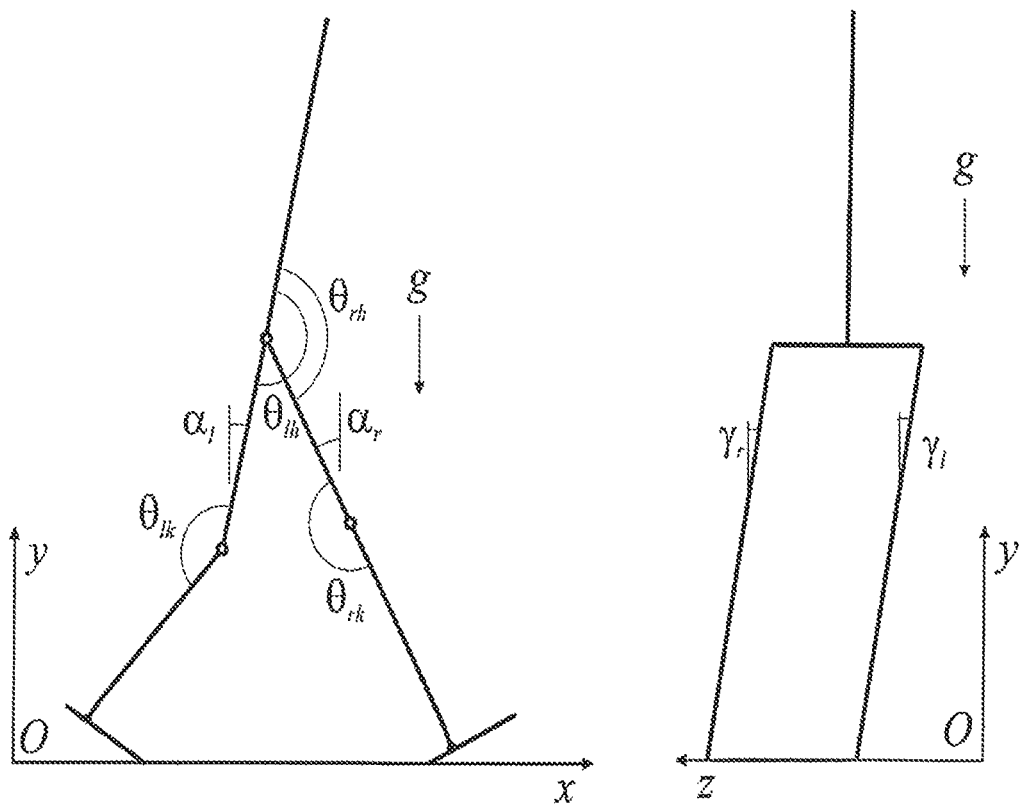
FIGS. 12A and 12B show angles in the sagittal and frontal planes, respectively, utilized for the operation for the controller of FIG. 11.

For example, in the case the previous step was small (i.e., the feet are relatively close together), the next step may be triggered by a larger thigh tilt (i.e., more clockwise movement of the forward thigh in the x-y plane in FIG. 12A). In the case the previous step was large (i.e., the feet are relatively far apart), the next step may be triggered by a smaller thigh tilt (i.e., less clockwise movement of the forward thigh). In another embodiment, the next step can be triggered by a change in thigh tilt, relative to, for example, the initial thigh tilt when entering the current double-support state. The sagittal plane thigh threshold for triggering the next step may also be inversely related to the angular velocity of the thigh in the sagittal plane, such that a larger angular velocity might reduce the tilt threshold (i.e., a larger angular velocity in the clockwise direction will require a smaller movement in the clockwise direction), while a smaller angular velocity might increase the threshold.

2.4.2 Transitions Between Walking and Standing

As depicted in FIG. 11, the exoskeleton controller consists of at least a standing state (i.e., right and left feet are essentially aligned in the sagittal plane) and at least one stepping state. In a preferred embodiment of the walking controller, the user must meet the previously described condition (on the sagittal plane thigh tilt) within a predetermined period of time in order to trigger the subsequent stepping state. In this embodiment of the walking controller, if the user does not trigger the subsequent stepping state within a predetermined period of time, the subsequent step (when triggered) will return the exoskeleton to the standing configuration (i.e., the next step will effectively be a half step rather than a full step, returning the exoskeleton to the standing state). In a preferred embodiment, the user receives a vibratory feedback for a short duration, when the period of time required to take the next full step has elapsed. This vibratory feedback informs the user that triggering the next step will be a half step that will return the user to the standing state. In a preferred embodiment, the half step motion is noticeably slower than the full step motion, which informs the user that the step is a half step.

In order to return to the stepping state from the standing state, the user can exceed a predetermined thigh tilt. Since the feet are together, the thigh tilt threshold can for example be based on the sagittal plane thigh tilt of a single leg, or the average thigh tilt of both legs. Further, in a preferred embodiment, the user must meet this tilt threshold for a predetermined period of time in order to enter the (right or left) stepping state. In one embodiment of the controller, the first step from the standing state is always either a right step or a left step. In another embodiment, the user can combine sagittal plane thigh tilt ($\alpha$'s in FIG. 12A) with frontal plane thigh tilt ($\gamma$'s in FIG. 12B), in order to determine which leg (right or left) will step first. For example, if a user meets a predetermined thigh tilt threshold in the sagittal plane, and also meets a predetermined thigh tilt in the frontal plane, the exoskeleton will enter a step with the leg that the user is "leaning" away from in the frontal plane (i.e., a frontal plane thigh tilt towards the right will trigger a left step, while a frontal plane thigh tilt towards the left will trigger a right step). In a preferred embodiment, the exoskeleton will generate a vibratory feedback to the user (i.e., will generate a vibration in the exoskeleton) when the user has met the threshold condition to enter the left or right stepping state. In a preferred embodiment, this vibratory feedback will continue until the predetermined period of time has lapsed and the step is triggered, or until the user no longer meets the threshold condition. This implementation notifies the user (with vibration) when he or she has met the condition to take a step, and provides a period of time in which the user can correct the thigh configuration, should he or she not want to trigger a step (i.e., not want to start walking).

2.4.3 Transitions Between Standing and Sitting

As depicted in FIG. 11, the exoskeleton controller consists of at least a sitting state and a standing state. In order to enter the sitting state from the standing state, the user can exceed a predetermined sagittal plane thigh tilt in the posterior direction (or counterclockwise direction in the sagittal plane in FIG. 12A). The thigh tilt can (for example) be based on the average sagittal plane thigh tilt of both legs. In a preferred embodiment, the user must meet this tilt threshold for a predetermined period of time in order to enter the sitting state. In a preferred embodiment, the exoskeleton will generate a vibratory feedback to the user (i.e., will generate a vibration in the exoskeleton) when the user has met the threshold condition to enter the sitting state. In a preferred embodiment, this vibratory feedback will continue until the predetermined period of time has lapsed and transition to the sitting state is triggered, or until the user no longer meets the threshold condition for sitting. This implementation notifies the user (with vibration) when he or she has met the condition to sit, and provides a period of time in which the user can correct the thigh configuration, should he or she not want to sit. Additionally, if the user has triggered the transition to sitting, yet does not wish to sit, he or she can switch back to the standing state based on the slowing or reversal of the thigh tilt in the sagittal plane. Specifically, the user can slow or reverse the transition from the standing to the sitting state with his or her arms, via his or her stability aid. If the sagittal thigh tilt velocity (of either or both thighs) falls below a given threshold, the exoskeleton can re-enter the standing state. Further, the exoskeleton can check the sagittal plane thigh tilt (of either or both thighs), and based on the thigh tilt, only allow a return to the standing state if the thigh tilt is less than some predetermined threshold (e.g., to ensure the user is more closely aligned with the vertical than the horizontal prior to returning to the standing state).

As shown in FIG. 11, the exoskeleton controller can also consist of at least a sitting state, a pre-standing state, and a standing state. In a preferred embodiment, the exoskeleton cannot transition directly from the sitting state to the standing state, but rather must transition from sitting to standing through the pre-standing state. The user must meet certain configuration thresholds to enter the pre-standing state from the sitting state. These configuration thresholds can be based on achieving knee flexion thresholds, hip flexion thresholds, or both. In one embodiment, both knees must be flexed beyond a predetermined threshold as a condition to enter pre-standing. In another embodiment, both hips must be flexed beyond a predetermined threshold as a condition to enter pre-standing. In a preferred embodiment, both knees must first meet flexion thresholds, followed by both hips meeting a flexion threshold, in order to enter the pre-standing state. In a preferred embodiment, in the sitting state, the exoskeleton can move each respective knee to the predetermined knee flexion angle when triggered by a change in the sagittal plane thigh tilt of the respective leg. In a preferred embodiment, entering the pre-standing state generates vibratory feedback to the user, which informs the user that the exoskeleton is in the pre-standing state. The vibratory feedback continues until the user moves the exoskeleton out of the pre-standing configuration thresholds (e.g., the hips are extended), or until the exoskeleton transitions from the pre-standing state to the standing state. A transition from the pre-standing state to the standing state can be triggered based on a substantial upward rotation of at least one thigh, indicated by a change in sagittal plane thigh tilt, or an angular velocity of at least one thigh in the sagittal plane, exceeding a predetermined threshold for a predetermined duration of time. These changes in thigh tilt or thigh angular velocity would be caused by the user pushing against the ground with his or her stability aid.

2.4.4 Transitions Between Walking and Stairs

As depicted in FIG. 11, the exoskeleton controller consists of at least a standing state and a stair ascent controller, where the stair ascent controller consists of at least a step-up state. The transition from the standing state to the step-up state is triggered based on the frontal plane thigh tilt exceeding a predetermined threshold angle for a predetermined duration of time. In a preferred embodiment, meeting this frontal plane tilt condition will generate a vibratory feedback to the user, until the step-up state is triggered, or until the condition is no longer met. In addition to frontal plane thigh tilt, the transition from standing to the step-up state can be based on a combination of frontal plane and sagittal plane thigh tilt. In one embodiment, the direction of frontal plane thigh tilt can determine which leg enters the step-up state. In another embodiment, the direction of frontal plane thigh tilt can determine whether the controller transitions from the standing state to a step-up state (for stair ascent), or to a step-down state (for stair descent). In one embodiment, the stair ascent controller consists of at least a step-up state and a step-to state. The step-up state raises the respective foot to the next stair tread, while the step-to state raises the user's body and trailing foot to the same stair tread. The final configuration of the step-to state is the standing state (on the stair tread above the previous stair). The transition from step-up state to step-to state can be determined based on the sagittal plane thigh tilt of at least one thigh exceeding a predetermined threshold. In one embodiment, once the controller has entered the stair ascent mode, the transition from standing to each subsequent step-up state is based on the thigh tilt of at least one thigh exceeding a predetermined threshold. In one embodiment the thigh tilt can be frontal plane tilt, while in another embodiment the thigh tilt can be sagittal plane tilt.

When in the stair ascent mode, the determination to leave the stair ascent mode can be made while in the standing state based on the frontal plane thigh tilt of at least one thigh exceeding a predetermined threshold angle for a predetermined duration of time. In a preferred embodiment, exceeding this thigh tilt threshold will generate a vibratory feedback to the user. In particular, a pattern of vibratory feedback can be used to inform the user that the exoskeleton is no longer in stair ascent mode.

As depicted in FIG. 11, the exoskeleton controller consists of at least one standing state and at least one stair descent mode, where the stair descent controller consists of at least a step-down state. The determination to enter the stair descent mode (i.e., the step-down state) from the standing state is based on the frontal plane thigh tilt of at least one thigh exceeding a predetermined threshold angle for a predetermined duration of time. The determination to enter stair descent can also be based on a combination of frontal and sagittal plane thigh tilts. In a preferred embodiment, the exoskeleton will generate vibratory feedback when these tilt thresholds have been met, until the step-down state is entered, or until the tilt thresholds are no longer met. Once in stair descent mode, subsequent switching from the standing state to the step-down state can be based on frontal or sagittal plane thigh tilt (without requiring a predetermined period of time, or issuing vibratory feedback). In a preferred embodiment, the subsequent triggering of the step-down state is based on the sagittal plane thigh tilt exceeding a predetermined threshold. In one embodiment, the stair descent controller consists of at least a step-down state and a step-to state. The step-down state flexes one knee, while lowering one foot to the next lower stair tread. The step-to state lowers the trailing foot to the same stair tread (and thus the step-to state ends in a standing state on one step below the previous stair tread). In this embodiment, transition from the step-down state to the step-to state can be based on at least one thigh tilt angle.

When in the stair descent mode, the determination to leave the stair descent mode can be made while in the standing state based on the frontal plane thigh tilt of at least one thigh exceeding a predetermined threshold angle for a predetermined duration of time. In a preferred embodiment, exceeding this thigh tilt threshold will generate a vibratory feedback to the user. In particular, a pattern of vibratory feedback can be used to inform the user that the exoskeleton is no longer in stair ascent mode.

In embodiments directed to switching from standing to stair ascent, stair ascent to standing, standing to stair descent, and stair descent to standing, a sustained frontal plane lean to one side (direction one) will switch from standing to stair ascent; a sustained frontal plane lean to the opposite side (direction two) will switch from stair ascent to standing; a sustained frontal plane lean in direction two will switch from standing to stair descent; and a sustained frontal plane lean in direction one will switch from stair descent to standing. In other words, a sustained lean to one side (e.g., the left side) will cause a general upward inflection in terrain, while a sustained lean to the opposite side (e.g., the right side) will cause a general downward inflection in terrain. In this embodiment, the first step will always be taken with a preferred leg (e.g., the right leg). Also, in these embodiments, vibratory feedback, via transducers, can provide an indication of meeting the condition to switch into the subsequent mode, and additional vibratory feedback can provide confirmation. Once in the respective stair ascent or descent states, proceeding with stair ascent or descent is then based on forward (i.e., sagittal plane) tilt of the thigh.

In some embodiments, the step-up state of the stair ascent mode and the step-down state of the stair descent mode each consists of two sub-states, which are a trajectory-controlled sub-state and a damping sub-state. The former bring the swing foot slightly above the next stair tread, while the latter allows the foot to settle on the stair tread, such that the control system need not know the precise stair height. In the case of the step-up state, the damping behavior is primarily in the swing leg, while in the case of the step-down state, the damping behavior is primarily in the stance leg. In a preferred embodiment, the exoskeleton system can estimate the step height following each step, and adjust the trajectory of the trajectory-controlled sub-state to more closely match the step height.

3. FUNCTIONAL ELECTRICAL STIMULATION

The orthosis described above can be supplemented with functional electrical stimulation (FES) of the user's muscles (i.e., using electrical stimulation to elicit contractions of the user's muscles). The FES can be controlled by the DES to provide as much movement as possible, with the remaining movement provided by the assistance device.

One methodology for providing the supplemental FES is as follows. First, the DES can be configured to obtain measures of the amount of motor torque required for a given movement without FES. Thereafter, the DES can utilize this measurement to estimate the timing and extent of the FES for a given muscle group. The DES can then increase or decrease the FES for that muscle group on a step by step basis to minimize the amount of torque required by the motor on the assistive device. Such a configuration allows a user undergoing rehabilitation to primarily rely on the orthosis during initial stages of rehabilitation and to reduce his dependence on the orthosis over time. Alternatively, in the case of a paraplegic, the FES can be used to stimulate muscle groups in the legs to cause their use. The resulting benefit would be two-fold. First, improved overall health is provided when the paraplegic user is allowed to bear weight on his legs and the muscles in the legs are caused to function, as discussed previously. Second, the amount of power needed for the orthosis is reduced. That is, as FES stimulates and causes the muscles in the legs to operate over time, more of the work for motion can be performed by the muscles instead of the orthosis.

Figure 13:
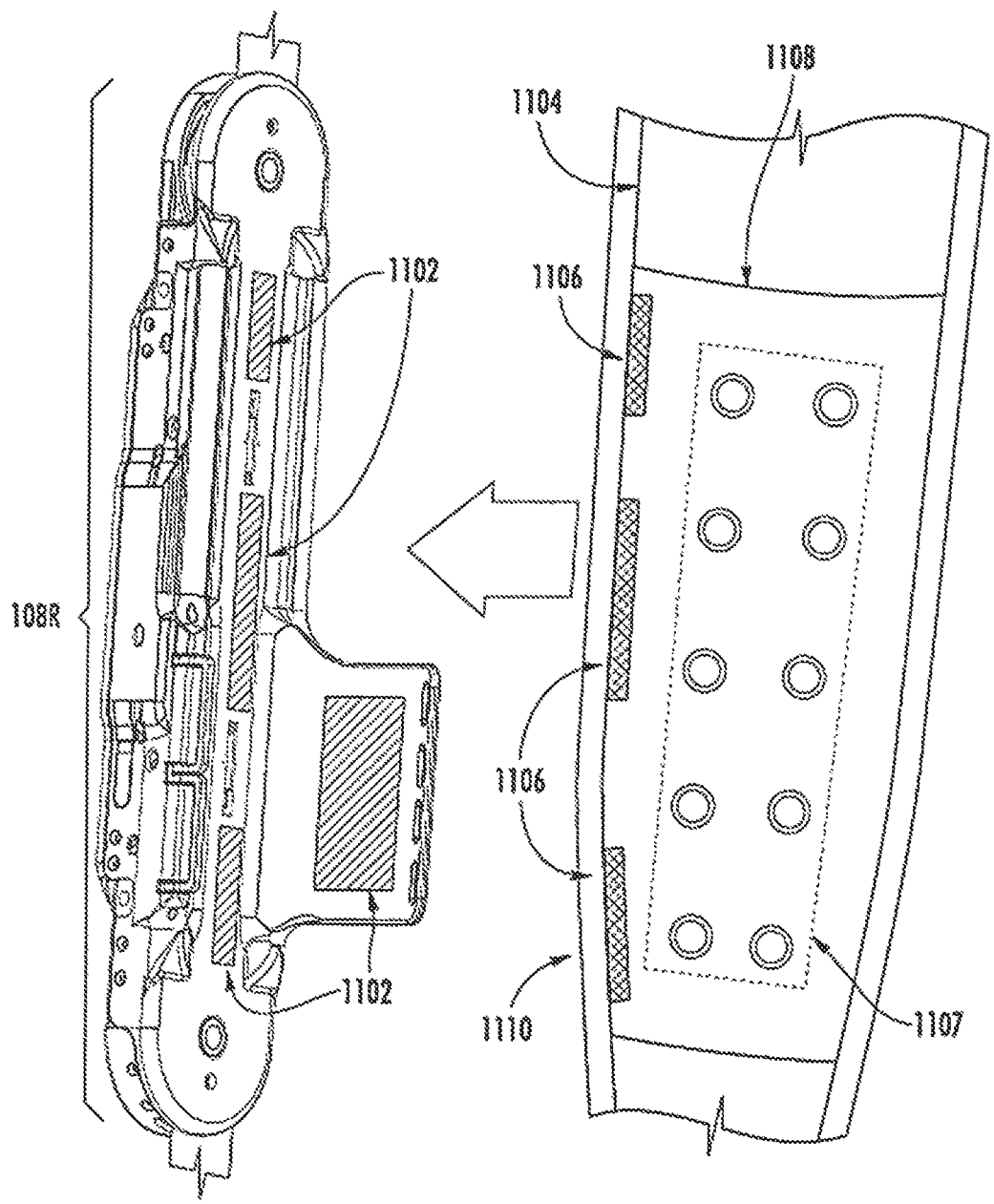
FIG. 13 is a schematic showing an exemplary arrangement for functional electrical stimulation in accordance with the various embodiments.

A general arrangement of the FES electrodes with respect to the orthosis is illustrated in FIG. 13. FIG. 13 is a schematic illustration for providing FES to the right thigh of a user using the right thigh segment 108R in FIGS. 1-4. Although only right thigh segment 108R is discussed herein, this is solely for ease of explanation. A similar configuration can be used to provide additional FES with the other segment in orthosis 100. To provide FES, the right thigh segment 108R is configured to include one or more FES source sites 1102 on the surfaces that will be facing or in contact a right thigh 1104 of the user. The arrangement of FES source sites 1102 in FIG. 13 is provided for illustrative purposes only. The FES source sites 1102 are configured to coincide with FES receive sites 1106 on the right thigh 1104, which then provide FES at electrodes 1107. Note that in some embodiments, it is not required that the FES receive sites 1106 coincide exactly with the placement of electrodes 1107 on the right thigh 1104. Rather, the FES receive sites 1106 can be configured to generally coincide with the FES source sites 1102 and to be in direct or indirect communication with the electrodes 1107 placed elsewhere on the right thigh 1104.

In the various embodiments, the size and arrangements of the FES source sites 1102, FES receive sites 1106, and the electrodes 1107 can vary in accordance with the configuration needed for FES and/or for a particular user. For example, the arrangement of electrodes 1107 can be selected based on which muscle groups are to receive FES. Accordingly, particular arrangements can be provided for FES of hamstring or quadriceps muscle groups. Other likely sites for electrode source sites and placement are on the anterior and posterior aspects of the shank segments 106R and 106L. However, the various embodiments are not limited in this regard and other locations can be used.

In some embodiments, the FES receive sites 1106 and the electrodes 1107 can be separately disposed on the right thigh 1104, via the use of adhesives or the like. In other embodiments, the FES receive sites 1106 and the electrodes 1107 can be disposed on the right thigh 1104 using a covering 1108 worn by the user over the right thigh 1104 and under the user's clothing 1110. In the various embodiments, the covering 1108 can be a garment, a splint, or any other type of device or apparel wearable by the user. Such a configuration can be advantageous as it reduces the need for the user to utilize adhesives or be concerned about proper alignment of all the electrode areas.

For example, in some embodiments, wireline connections can be provided. That is, the FES source sites 1102 can be directly wired to the FES receive sites 1106. In such a wireline configuration, it would not be necessary to include coinciding FES source sites 1102. Rather, wires could be run from one to the FES source sites 1102 to each of the FES receive sites 1106. In other wireline embodiments, The FES source sites 1102 could include needle-type electrodes which mate with electrical contacts in the FES receive sites 1106. In such a configuration, the needle type electrodes would be configured to pierce clothing 1110 covering the FES receive sites 1106 and thus transmits current through the clothing. However, the various embodiments are not limited to wireline methods and can also include wireless FES methods. For example, mutual inductance can be used to transmit the FES current from the FES source sites 1102 through the user's clothing 1110 to the FES receive sites 1106 and on to electrodes 1107. In such embodiments, the covering 1108 can include features that locates the FES receive sites 1106 relative to the FES source sites 1102 through the clothing 1110. The FES source sites 1102 would then contain a primary coil, while the FES receive sites 1106 contain a secondary coil, such that the FES is transmitted through the clothing without wires. Alternatively, the covering 1108 could include a separate power supply, an FES signal generator, and a transceiver for receiving signals from the orthosis, causing the FES signals to be generated and applied to the user.

4. EXAMPLES

The examples shown here are not intended to limit the various embodiments. Rather they are presented solely for illustrative purposes.

4.1 Preliminary Evaluation

In a first series of tests, the previously described orthosis and controller was implemented on a paraplegic subject in order to substantiate the ability of a powered orthosis in accordance with the various embodiments to provide gait assistance. Table 3 shows a mass breakdown of the resulting orthosis, showing that a light-weight orthosis was provided.

TABLE 3

Mass Breakdown of Orthosis

| Component | Mass (kg) | Mass Distribution |
| --- | --- | --- |
| Joint Actuation | 3.57 | 30% |
| Thigh Frames | 4.08 | 34% |
| Hip Brace | 2.10 | 17% |
| Shank Frames | 1.09 | 9% |
| Battery | 0.68 | 6% |
| Electronics | 0.50 | 4% |
| Total | 12.02 | 100% |

The subject for the first tests was a 35-year-old male (1.85 m, 73 kg) with a T10 complete injury, 8 years post injury. The evaluations described herein were conducted within a standard set of parallel bars. For the data presented below, the evaluation protocol was as follows. The subject stood from a wheelchair with footrests removed by issuing a "stand" voice command. Note that the footrests, if not removed, would obstruct the subject's ability to bring his feet close to the chair, and therefore would impede his ability to transition from sitting to standing. Once comfortable standing, the subject issued either a "left-step" or "right-step" voice command, and subsequently, a "step" voice command to initiate subsequent steps. Once near the end of the parallel bars, the subject issued a "half-step" command, which returned him to the standing configuration. The subject then turned in place in the parallel bars by lifting his weight with his arms and incrementally twisting around in order to walk in the opposite direction. This process repeated, typically for four to eight lengths of the parallel bars, at which point the subject sat (in his wheelchair, by issuing a "sit" voice command), so that data from the walking trial could be recorded.

Figure 14:
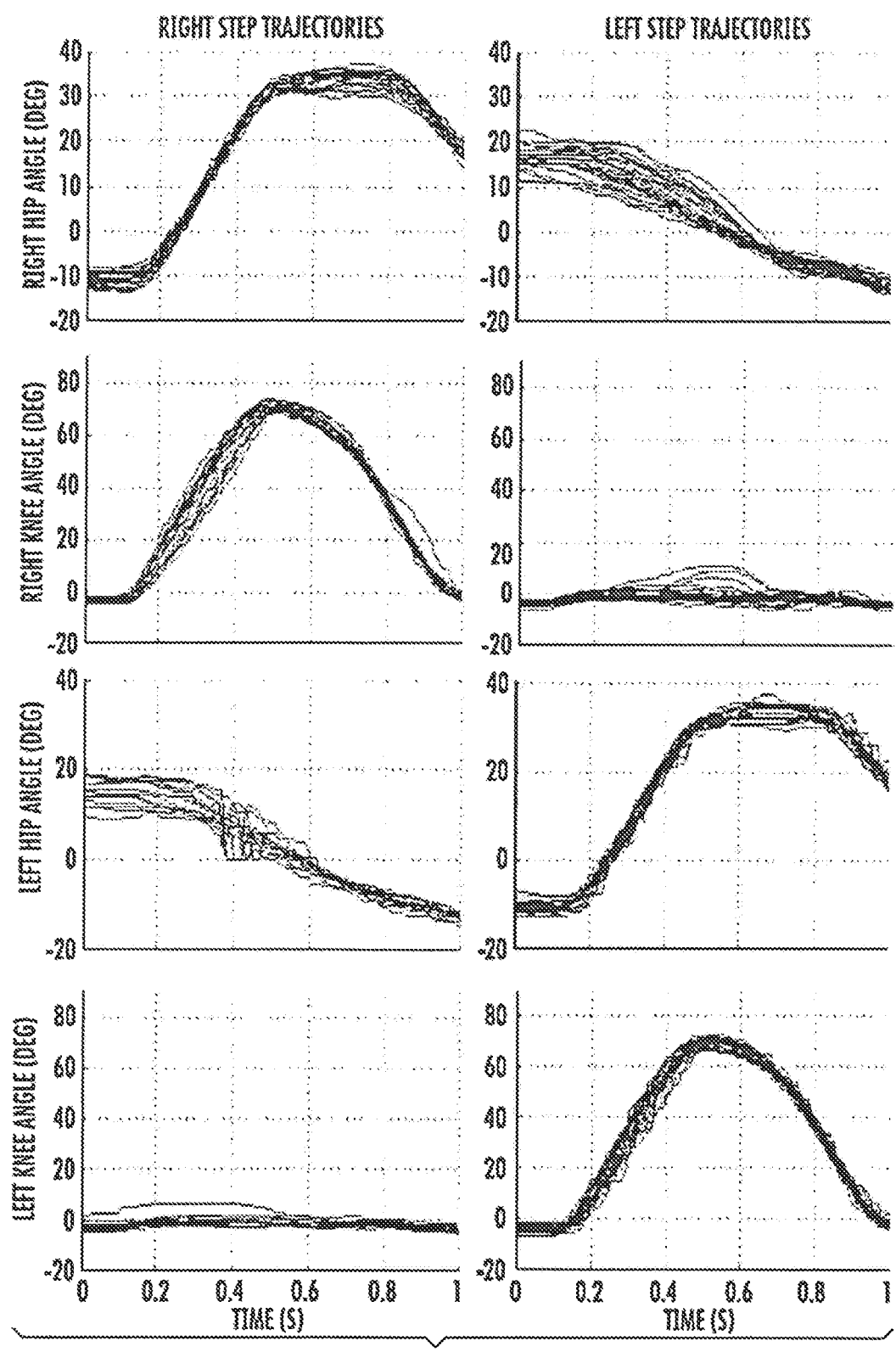
FIGS. 14 and 15 shows measured joint angle data for each of the joints, as a function of time, from 23 right steps and 23 left steps, overlaid onto the same plot.
Figure 15:
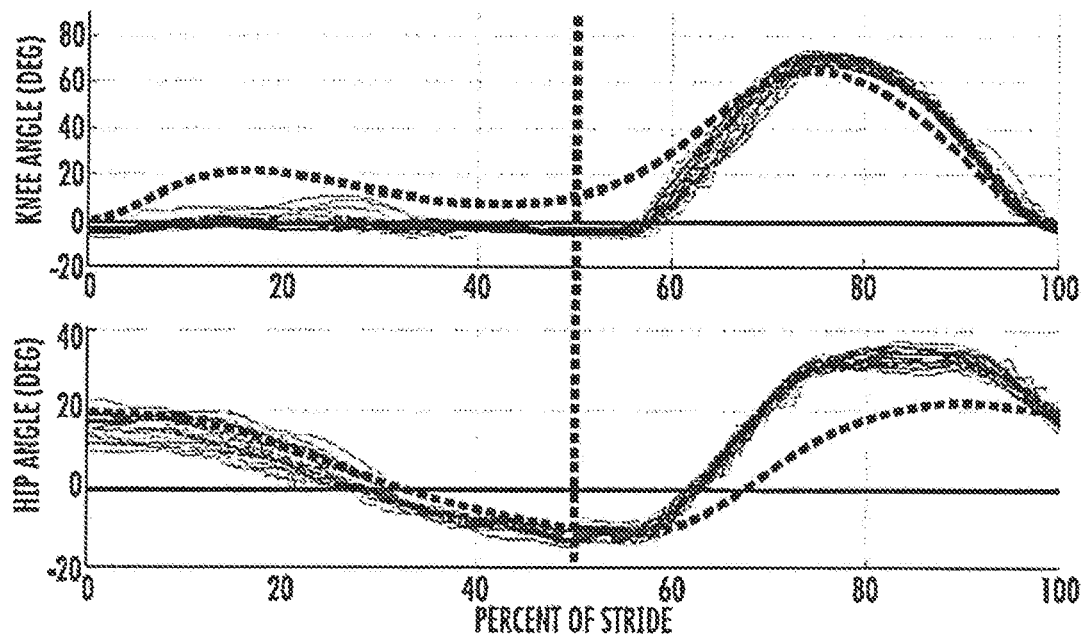

FIG. 14 shows measured joint angle data for each of the joints, as a function of time, from 23 right steps and 23 left steps, overlaid onto the same plot. Note that an approximate one-second delay exists between each right and left step, during which time the subject adjusted his upper body in preparation for commanding the next step. FIG. 15 shows the same data shown in FIG. 14, with the delay between steps replaced with a vertical dashed line (which indicates a discontinuity in time), with the time base replaced with a percent stride base, and with the left and right joint angles overlaid onto the same plots. In this manner, the knee and hip joint angles can be qualitatively compared to standard joint kinematics during walking, which is typically represented as a function of stride. These normal biomechanical trajectories are also plotted in FIG. 15 as dashed lines. The repeatability of the joint angle data over these 23 strides, and the similarity of such data to normal biomechanics (particularly with respect to the amplitude of knee flexion, and the amplitude of hip flexion and extension), indicate that the powered orthosis is able to provide appropriate and repeatable gait assistance to the user during walking. The gait represented by this data is characterized by an average overground walking speed of 0.22 m/s (0.8 km/hr or 0.5 mi/hr).

Figure 16:
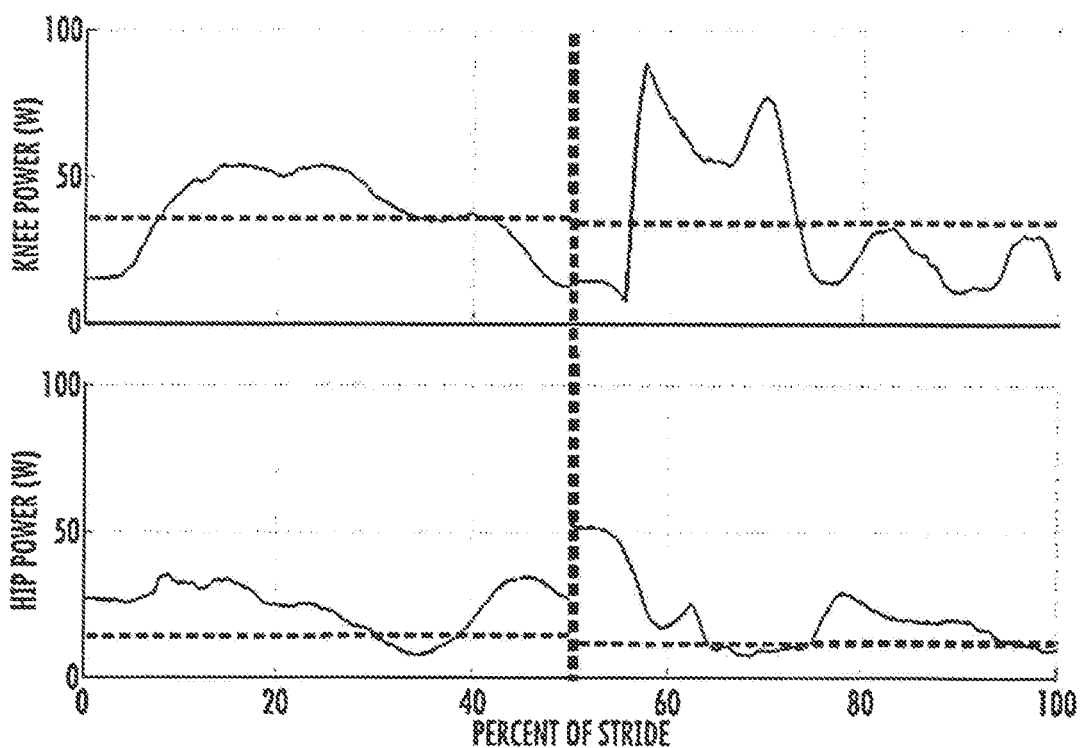
FIG. 16 shows power use as a function of stride for the data in FIG. 13.

Electrical power consumption was recorded during the walking represented by FIGS. 14 and 15. The electrical power required by the servoamplifiers, corresponding to the data shown in FIG. 15, is shown averaged over all 46 steps (or 23 strides) in FIG. 16. As shown in FIG. 16, there is an average power consumption of approximately 35 W for each knee actuator (during the active stride), and approximately 22 W for each hip actuator (during the stride). In addition to requiring electrical power during right and left steps, the joint actuators also used power to maintain joint stiffness in the double support states (i.e., while the subject shifted his weight to prepare for the next step). For the 46 step sequence previously described, the total electrical power required by each actuator was 27 W on average for each knee motor and 21 W on average for each hip motor during the swing phase of gait, and 26 W and 29 W of average power for the knee and hip motors, respectively, during the stance phase of gait. The knee brakes additionally required on average approximately 7 W of electrical power during swing, but did not require any power during stance (i.e., they are normally locked brakes). Finally, the average electrical power required by the remainder of the distributed embedded system was measured as 7.2 W. The average measured electrical power consumption for each component and each phase of the walking cycle is summarized in Table 4.

TABLE 4

Orthosis Electrical Power Consumption

| Component | Power During Stepping (W) | Power Between Steps (W) | *Average Power During Walking (W) |
| --- | --- | --- | --- |
| Swing Knee Motor | 34.8 | 19.6 | 27.2 |
| Stance Knee Motor | 35.6 | 16.5 | 26.1 |
| Swing Hip Motor | 21.4 | 19.8 | 20.6 |
| Stance Hip Motor | 23.9 | 34.0 | 29.0 |
| Embedded Electronics | 7.2 | 7.2 | 7.2 |
| Swing Knee Brake | 13.5 | 0 | 6.7 |
| Stance Knee Brake | 0 | 0 | 0 |
| Total | 136.4 | 97.1 | 116.8 |

*Average power with a one-second pause between steps (i.e., steps are being taken during 50% of the time during "walking")

With a one-second average pause between steps (corresponding to the 0.22 m/s walking data represented by FIG. 15), the total electrical power required by the system was 117 W. Recall that the battery pack included in the powered orthosis prototype described herein is a 680 g lithium polymer battery with a 115 W-hr capacity. Based on the walking data of FIG. 16 and Table 3, the battery would provide approximately one hour of continuous walking between charges. At the previously stated (measured) average overground speed of 0.8 km/hr (0.5 mi/hr), the powered orthosis would provide a range of approximately 0.8 km (0.5 mi) between battery charges. Note that the range could be easily increased, if desired, without incurring a significant mass penalty, by increasing the size of the battery, which currently constitutes 6% of the system mass (see Table 3). For example, doubling the size of the battery pack would double the range and result in an overall device mass of 12.7 kg, as opposed to 12 kg, as implemented here.

A digital sound level meter was also used while walking with the orthosis to evaluate noise. The average sound level, as measured one meter away from the orthosis, was approximately 55±2 dBA (with an ambient noise level of 38 dBA).

4.2 Assessing Suitability of the Control System

In a second set of tests, the ability of the above-described system to enable a user to autonomously perform the basic movements associated with legged mobility (i.e., sitting, standing, and level walking) was assessed in trials conducted with a paraplegic subject. The subject was a 35-year-old male (1.85 m, 73 kg) with a T10 motor and sensory complete injury (i.e., ASIA A), 9 years post injury. All data presented here corresponds to walking conducted using a walker as a stability aid. The data for these tests is shown in FIG. 17.

Figure 17:
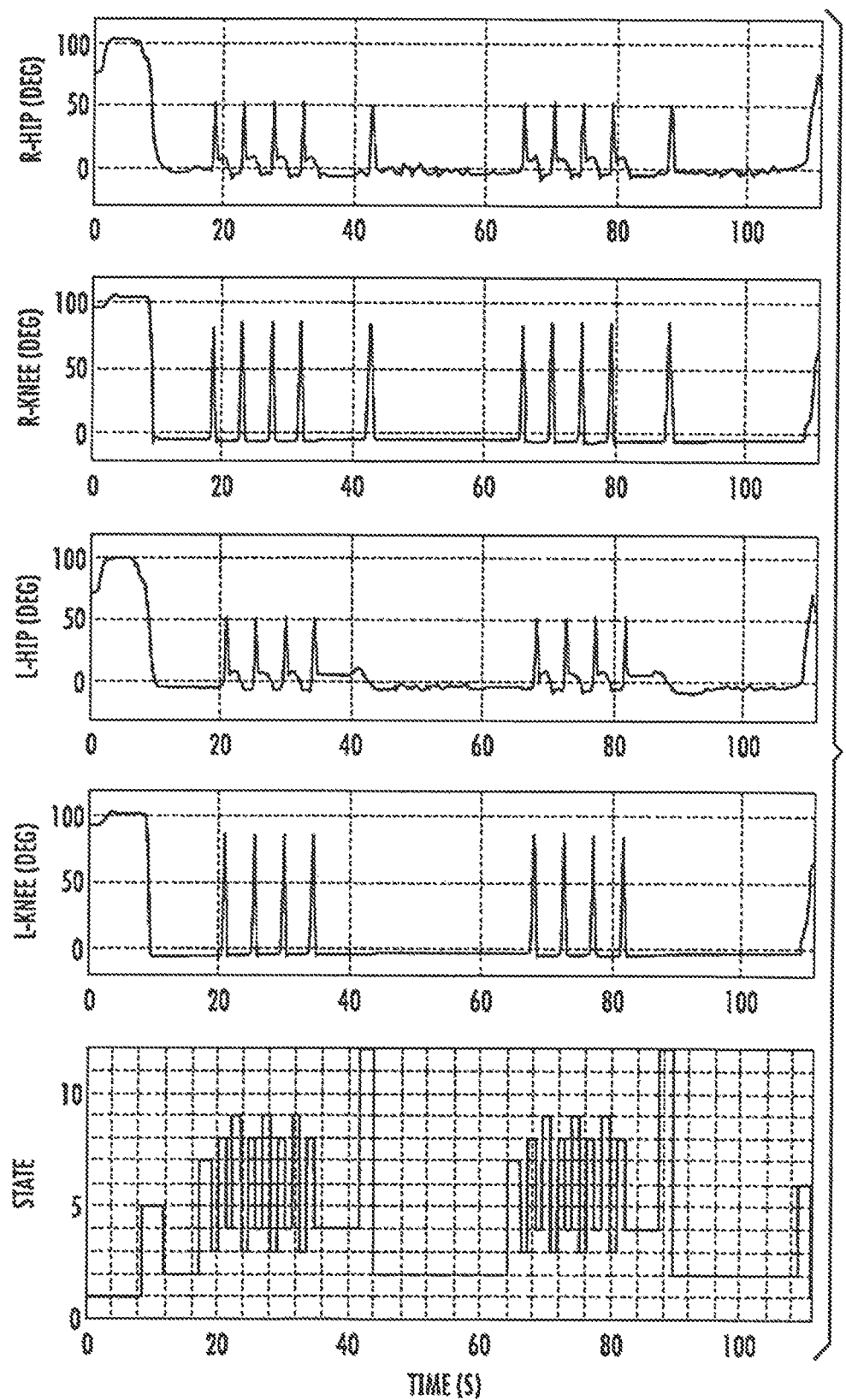
FIG. 17 shows joint angles (left and right hip, left and right knee) and state, as a function of time, for a test subject.

FIG. 17 shows joint angles (left and right hip, left and right knee) and state, as a function of time, for the above-identified the subject. The ability of the powered orthosis and control architecture to provide autonomously commanded sitting, standing, and walking was assessed by having the subject autonomously perform a timed-up-and-go (TUG) test. The TUG test is a standard clinical measure for assessing legged mobility. In this test, the subject starts seated in a chair, and given a start command, stands up, walks forward three meters, turns around in place, walks back to the starting point, and sits down in the chair. In order to assess the ability of the subject to autonomously control movements of the orthosis, this test was repeated a number of times, until the subject was comfortable performing the test. Once comfortable with the task, the subject was asked to repeat the TUG test three times. The set of data that corresponds to the third of these three TUG tests is the data shown in FIG. 17.

As shown in FIG. 17, the data shows the right and left hip and knee joint angles corresponding to this TUG test, along with the corresponding states of the FSM. In the sequence, the user starts in the sitting state (S1), after which the system enters the sitting to standing mode (S5), in which both hips and both knees provide torques to facilitate joint extension. Following S5, the state history depicts a series of consecutive steps, followed by a period of standing (S2), during which the subject turned in place, with the aid of the walker. The first series of steps is then followed by a second series, during which the subject returned to the chair. Once at the chair, the subject again entered standing mode (S2), allowing the subject to turn in place, prior to returning to a seated position in the chair.

Figure 18A:
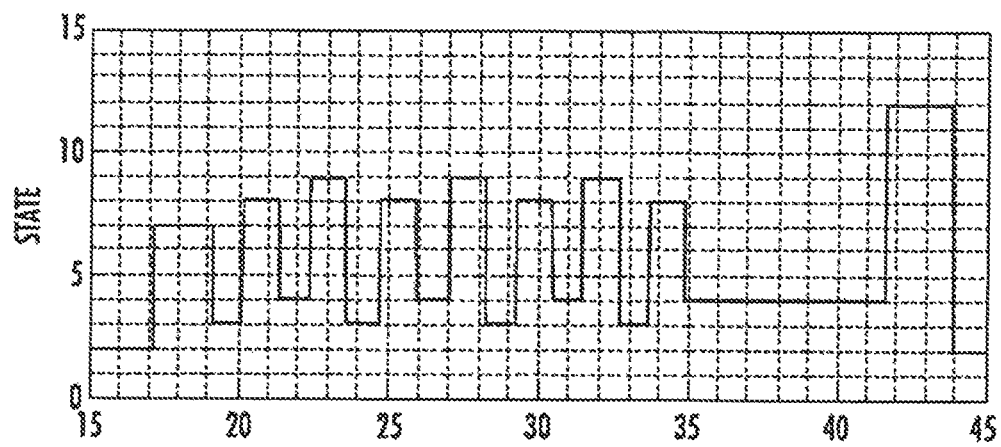
FIG. 18A shows the system state for several steps (of slightly varying length), as a function of time.
Figure 18B:
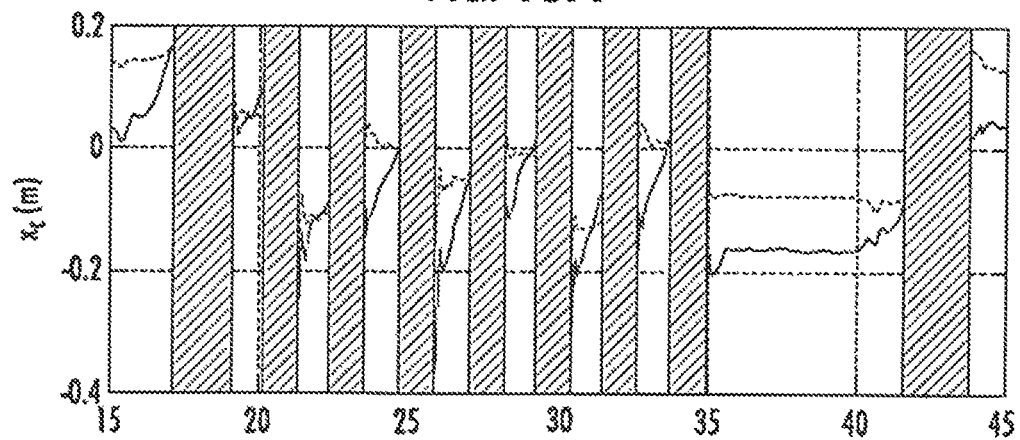
FIG. 18B shows the estimated CoP (Xc) (solid line) and the CoP switching threshold (Xĉ) (dashed line) for the same steps as in FIG. 18A.
Figure 18C:
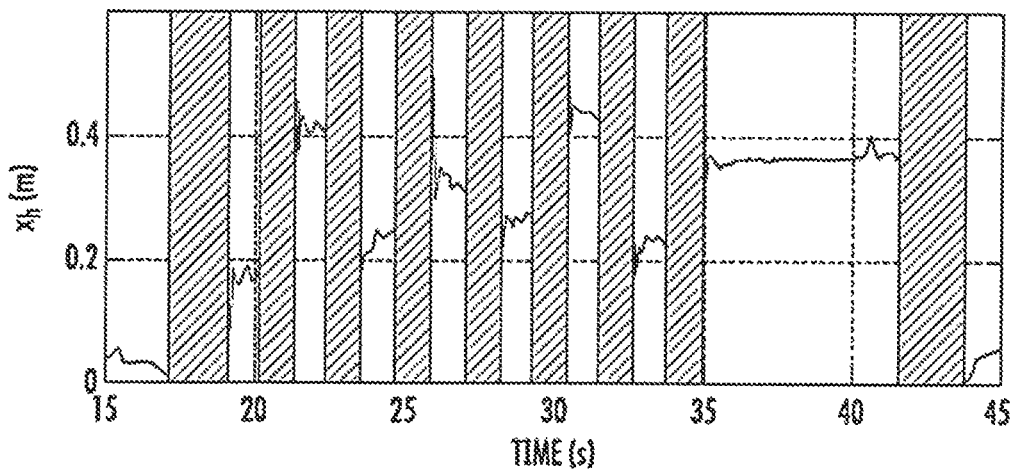
FIG. 18C shows the estimate of step length (Xh) for the same steps in FIGS. 18A and 18B.

Recall that the threshold for the CoP during walking is function of the step length. FIG. 18A shows the system state for several steps (of slightly varying length), as a function of time. FIG. 16B shows the estimated CoP ($X_c$) (solid line) and the CoP switching threshold ($X_{\tilde{c}}$) (dashed line) for the same steps as in FIG. 18A. FIG. 18C shows the estimate of step length ($X_h$) for the same steps in FIGS. 18A and 18B. As seen in the FIGS. 18A-18C, the CoP threshold ($X_c$) varies with step length ($X_h$). In general, when the CoP ($X_c$) exceeds the threshold at the end of the swing phase trajectory, the controller will switch immediately to the contralateral swing phase (i.e., switching between S8 and S9). If the CoP does not cross the CoP threshold at the end of swing phase, the controller will remain in the respective double support phase (S3 or S4) until the user shifts the CoP to cross the CoP threshold.

Figure 19A:
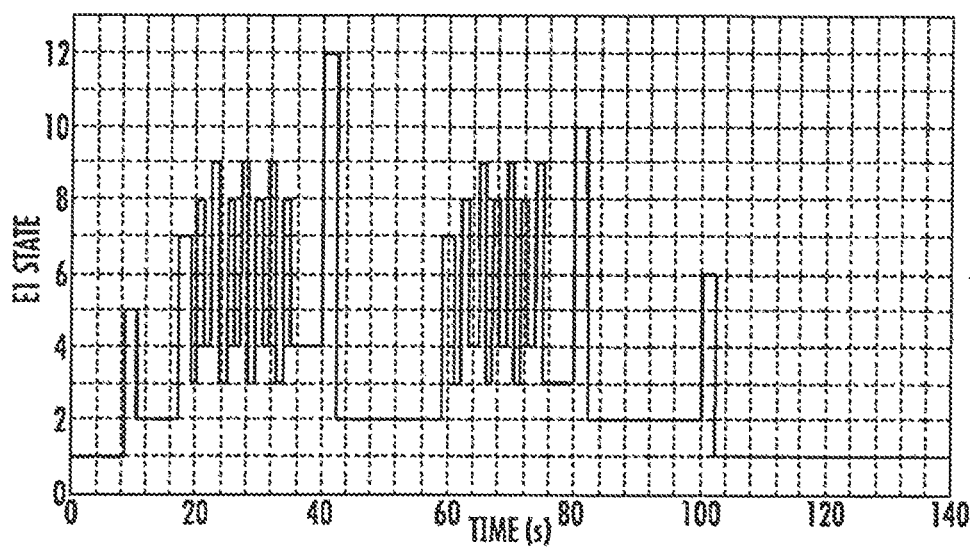
FIGS. 19A, 19B, and 19C presents the sequences of finite states corresponding to each of first, second, and third TUG tests, respectively.
Figure 19B:
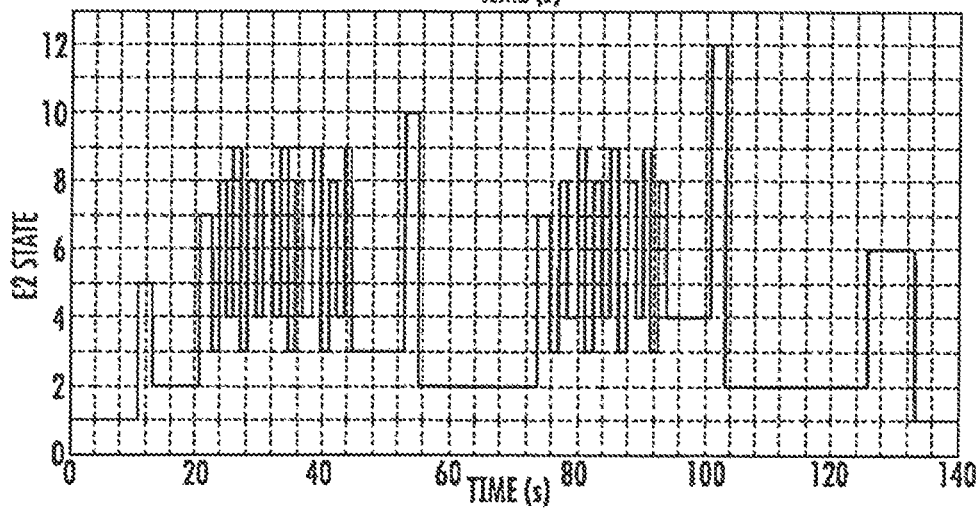
Figure 19C:
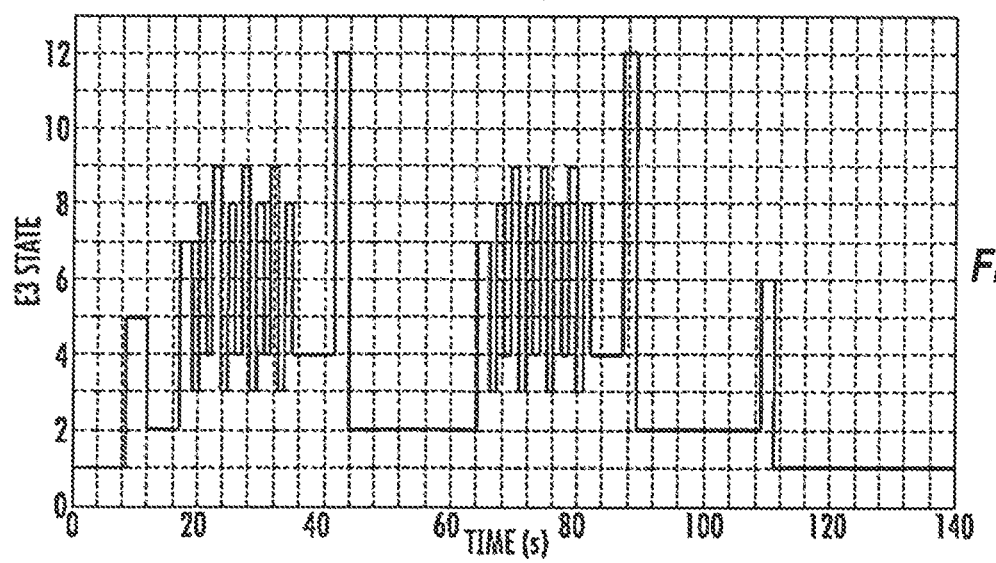

FIGS. 19A, 19B, and 19C presents the sequences of finite states corresponding to each of the first, second, and third TUG tests, respectively. The subject completed the three tests in 103, 128, and 112 s, respectively. The average time to complete the sequence was 114 s, with a standard deviation of 8.6 s (7.5%). The consistency between trials (i.e., standard deviation of ±7.5%) indicates that the control approach described above appears to provide a repeatable means for the subject to control the basic movements associated with legged mobility.

4.3 Assessing Impact to Paraplegic

The previously described orthosis prototype and control interface were implemented on a single paraplegic subject to characterize its performance in terms of the standard TUG test and a Ten Meter Walk Test (TMWT). The subject was a 35 year-old male, 9 years post-injury, 1.85 m tall, and with a body mass of 73 kg. Each of the walking test protocols was performed three times using a walker for stability and three times using forearm crutches for stability. To understand the subject's physical exertion using the device, heart rate measurements were recorded at rest before each test and subsequently recorded 30 seconds after completion of each test. The subject was also asked to rate his perceived level of exertion according to the Borg scale.

For comparison, the subject then repeated the tests with his own long-leg braces and a walker. Traditional long leg braces are used both in reciprocal gait and swing-through gait (the latter typically with a spreader bar used to constrain the feet to move together) and therefore the tests were conducted in both walking patterns with the long leg braces. Heart rate measurements and Borg ratings were similarly taken.

Figure 20:
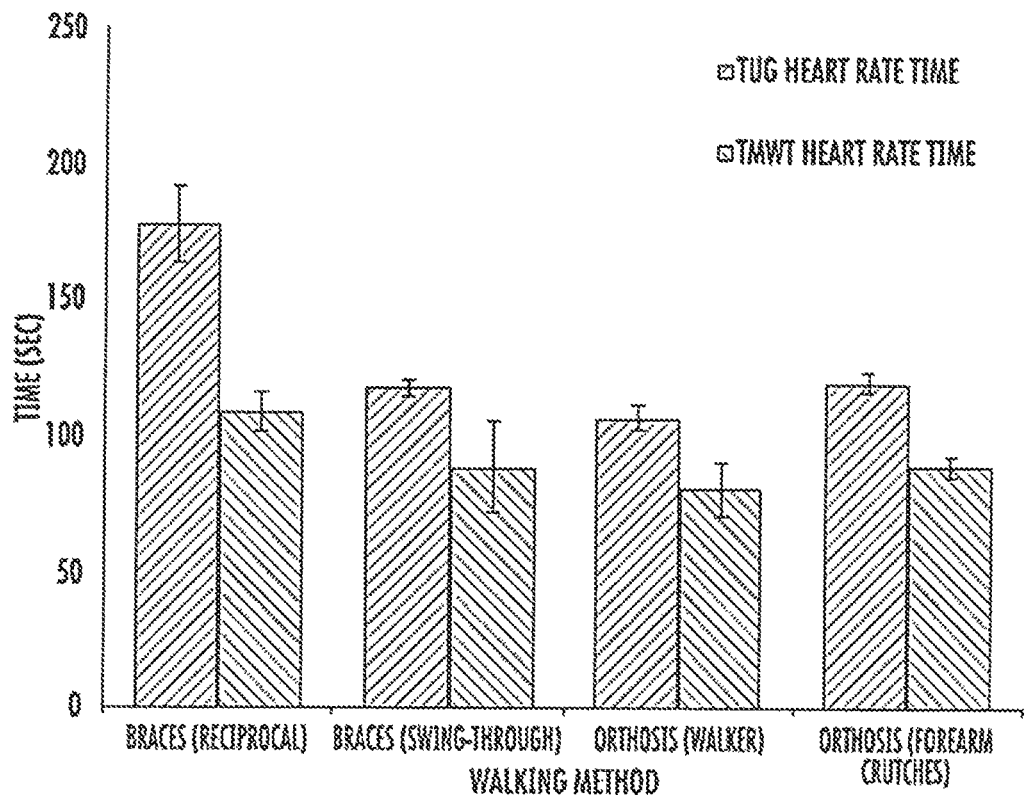
FIG. 20 graphically shows the results of TUG heart rate and TMWT heart rate for a subject using various walking methods.

Walking in the powered orthosis with a walker yielded the fastest times in both the TUG test and the TMWT. Both the long leg braces in swing-through gait and the powered orthosis with forearm crutches were about 10% slower in each test. The slowest times were recorded with the long leg braces in reciprocal gait, which were 66% slower in TUG testing and 35% slower in TMWT testing than the times achieved with the powered orthosis and walker. The results of the timed walking tests are shown graphically in FIG. 20.

Heart rate data from before and after the tests indicated the smallest user exertion while walking in the orthosis with forearm crutches, with only an average 3.9% rise in heart rate during TUG and a 1.2% decrease during TMWT. Performing the tests with the orthosis and a walker required slightly more user effort, indicated by an average 10.1% increase during TUG and a 5.4% increase during TMWT. The long leg braces in swing-through gait required significantly more user exertion, resulting in an average 19.0% increase in heart rate during TUG and 16.1% increase during TMWT. The highest level of user exertion was seen during testing with the long leg braces in reciprocal gait, with an average 41.8% increase in heart rate during TUG and an 18.4% increase during TMWT. A direct correlation was seen between heart rate increase and the user's perceived exertion. He assigned a Borg scale score of 9 to walking with the orthosis and crutches, 10 to the orthosis and walker, 13 to the long leg braces with swing-through gait, and 14 to the long leg braces with reciprocal gait. The Borg RPE scale is provided in Table 5.

TABLE 5

Borg Rating of Perceived Exertion Scale

| SCORE | DESCRIPTION |
|---|---|
| 6 | NO EXERTION AT ALL |
| 7 | |
| 7.5 | EXTREMELY LIGHT |
| 8 | |
| 9* | VERY LIGHT |
| 10 | |
| 11 | LIGHT |
| 12 | |
| 13** | SOMEWHAT HARD |
| 14 | |
| 15 | HARD (HEAVY) |
| 16 | |
| 17*** | VERY HARD |
| 18 | |
| 19**** | EXTREMELY HARD |
| 20 | MAXIMAL EXERTION |

A "9" corresponds to "very light" exercise. For a healthy user, it is like walking slowly at his or her own pace for some minutes. A "13" on the scale is "somewhat hard" exercise, but it still feels OK to continue. A "17" or "very hard" is very strenuous. A healthy user can still go on, but he or she really has to push him- or herself. It feels very heavy, and the user is very tired. A "19" on the scale is an extremely strenuous exercise level. For most people this is the most strenuous exercise they have ever experienced.

Figure 21:
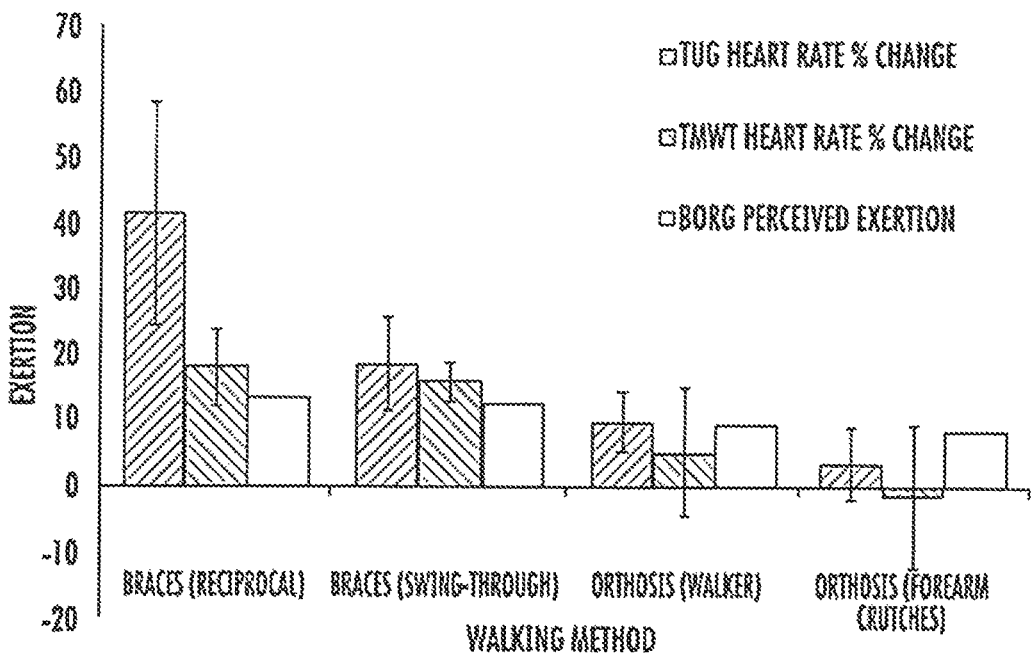
FIG. 21 graphically shows TUG heart rate % change, TMWT heart rate % change, and Borg perceived exertion for a subject using various walking methods

The heart rate data (in terms of percent of change) and Borg ratings from timed walking tests are shown graphically in FIG. 21. A summary of the TUG and TMWT scores, heart rate changes, and Borg ratings is provided in Table 6.

TABLE 6

Summary of Timed Walking Test Data

| WALKING METHOD | TUG TIME (SECONDS) | HEART RATE CHANGE (%) | TMWT TIME (SECONDS) | HEART RATE CHANGE (%) | BORG RATING |
|---|---|---|---|---|---|
| LL BRACES + WALKER (RECIPROCAL) | 178 ± 14 | 41.8 ± 17.1 | 109 ± 7 | 18.4 ± 5.9 | 14 |
| LL BRACES + WALKER (SWING-THROUGH) | 118 ± 3 | 19.0 ± 7.2 | 89 ± 17 | 16.1 ± 2.9 | 13 |

TABLE 6-continued

Summary of Timed Walking Test Data

| WALKING METHOD | TUG TIME (SECONDS) | HEART RATE CHANGE (%) | TMWT TIME (SECONDS) | HEART RATE CHANGE (%) | BORG RATING |
|---|---|---|---|---|---|
| POWERED ORTHOSIS + WALKER | 107 ± 5 | 10.1 ± 4.6 | 81 ± 10 | 5.4 ± 9.5 | 10 |
| POWERED ORTHOSIS + FOREARM CRUTCHES | 120 ± 4 | 3.9 ± 5.4 | 89 ± 4 | −1.2 ± 10.7 | 09 |

Results are average values from three experiments in each walking method.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method of controlling an apparatus comprising an exoskeleton having a hip segment, at least one lower limb, and a plurality of sensors for generating signals indicating a current motion and a current arrangement of at least the exoskeleton, the at least one lower limb comprising a thigh segment and a shank segment for coupling to a lateral surface of a leg of a user, a first powered joint configured for providing motion of the thigh segment relative to the hip segment, and a second powered joint configured for providing motion of the shank segment relative to the thigh segment, at least a portion of the plurality of sensors being disposed on the at least one lower limb, the method comprising:
receiving the signals from the plurality of sensors;
based on the signals, determining a current state of the exoskeleton;
estimating a location of a center of pressure of a combination of the user and the exoskeleton based on the signals and inertial properties of the user;
inferring a current intent of the user based on at least the current state of the exoskeleton and a location of the center of pressure relative to at least one reference point for the exoskeleton;
determining a next state for the exoskeleton based at least on the current state and the current intent; and
generating control signals to cause the exoskeleton to transition to the next state.

2. The method of claim 1, further comprising generating at least one of a tactile indicia, a visual indicia, or an audio indicia to provide feedback to the user regarding the next state.

3. The method of claim 1, wherein the step of determining the next state further comprises selecting one of a plurality of activity modes and a state in the one of the plurality of activity modes.

4. The method of claim 1, further comprising generating functional electrical stimulation (FES) signals for the at least one lower limb of the user.

5. The method of claim 4, wherein the step of generating the control signals further comprises, for each of the first powered joint and the second powered joint:
determining a first amount of torque required to transition to the next state,
monitoring a second amount of torque being generated in response to the FES signals, and
configuring the control signals to cause the movement of the exoskeleton to generate a third amount of torque equal to a difference between the first and the second amounts of torque.

6. The method of claim 1, wherein the inertial properties of the user comprise a center of mass for each of the segments in the at least one lower limb of the user and a center of mass for a combination of a head, arms, and trunk of the user.

7. The method of claim 1, wherein the signals correspond to an angle of the hip segment relative to the thigh segment, an angle of the shank segment relative to the thigh segment, and an angle of the thigh segment relative to a direction of gravity.

8. The method of claim 1, wherein the at least one reference point comprises a pre-defined portion of the exoskeleton.

9. The method of claim 1, wherein the at least one reference point comprises a location portion of the exoskeleton.

10. A computer-readable medium having computer-readable code stored thereon executable by a computer controlling an exoskeleton, the exoskeleton having a hip segment, at least one lower limb, and a plurality of sensors for generating signals indicating a current motion and a current arrangement of the exoskeleton, the at least one lower limb comprising a thigh segment and a shank segment for coupling to a lateral surface of a leg of a user, a first powered joint configured for providing motion of the thigh segment relative to the hip segment, and a second powered joint configured for providing motion of the shank segment relative to the thigh segment, at least a portion of the plurality of sensors being disposed on the at least one lower limb, the computer-readable code comprising a plurality of instructions causing the computer to perform steps:
receiving the signals from the plurality of sensors;
based on the signals, determining a current state of the exoskeleton;
estimating a location of a center of pressure of a combination of the user and the exoskeleton based on the signals and inertial properties of the user;
inferring a current intent of the user based on at least the current state of the exoskeleton and a location of the center of pressure relative to at least one reference point for the exoskeleton;
determining a next state for the exoskeleton based at least on the current state and the current intent; and
generating control signals to cause the exoskeleton to transition to the next state.

11. The computer-readable medium of claim 10, the computer-readable code further comprising instructions for causing the computer to generate at least one of a tactile indicia, a visual indicia, or an audio indicia to provide feedback to the user regarding the next state.

12. The computer-readable medium of claim 10, wherein the step of determining the next state further comprises selecting one of a plurality of activity modes and a state in the one of the plurality of activity modes.

13. The computer-readable medium of claim 10, the computer-readable code further comprising instructions for causing the computer to generate functional electrical stimulation (FES) signals for the at least one lower limb of the user.

14. The computer-readable medium of claim 13, wherein the computer-readable code further comprising instructions for causing the computer, for each of the first powered joint and the second powered joint:
to determine a first amount of torque required to transition to the next state,
to monitor a second amount of torque being generated in response to the FES signals, and
to configure the control signals to cause movement of the exoskeleton to generate a third amount of torque equal to a difference between the first and the second amounts of torque.

15. The computer-readable medium of claim 10, wherein the inertial properties of the user comprise a center of mass for each of the segments in the at least one lower limb of the user and a center of mass for a combination of a head, arms, and trunk of the user.

16. The computer-readable medium of claim 10, wherein the signals correspond to an angle of the hip segment relative to the thigh segment, an angle of the shank segment relative to the thigh segment, and an angle of the thigh segment relative to a direction of gravity.

17. The computer-readable medium of claim 10, wherein the at least one reference point comprises a pre-defined portion of the exoskeleton.

* * * * *